(12) United States Patent
Bermudes

(10) Patent No.: US 10,286,051 B1
(45) Date of Patent: May 14, 2019

(54) MODIFIED BACTERIA HAVING IMPROVED PHARMACOKINETICS AND TUMOR COLONIZATION ENHANCING ANTITUMOR ACTIVITY

(71) Applicant: David Gordon Bermudes, Woodland Hills, CA (US)

(72) Inventor: David Gordon Bermudes, Woodland Hills, CA (US)

(*) Notice: Subject to any disclaimer, the term of this patent is extended or adjusted under 35 U.S.C. 154(b) by 0 days.

(21) Appl. No.: 15/482,170

(22) Filed: Apr. 7, 2017

Related U.S. Application Data

(62) Division of application No. 14/858,810, filed on Sep. 18, 2015, now Pat. No. 9,616,114.

(60) Provisional application No. 62/052,252, filed on Sep. 18, 2014.

(51) Int. Cl.
*C12N 15/74* (2006.01)
*A61K 39/00* (2006.01)

(52) U.S. Cl.
CPC .......... *A61K 39/0011* (2013.01); *C12N 15/74* (2013.01); *A61K 2039/52* (2013.01); *A61K 2039/585* (2013.01)

(58) Field of Classification Search
CPC .......... A61K 2039/52; A61K 2039/585; A61K 35/74; A61K 39/0011; A61L 2039/585; C11D 11/0082; C11D 3/0052; C11D 3/046; C11D 3/10; C12N 15/74
See application file for complete search history.

(56) References Cited

U.S. PATENT DOCUMENTS 9,616,114 B1 * 4/2017 Bermudes .......... A61K 39/0011

OTHER PUBLICATIONS

Toso et al, J Clin Oncol. Jan. 1, 2002;20(1):142-52.*
Meir et al., 2001, Proc Am Soc Clin Oncol 20: abstr 1043.*
Nemunaitis et al., 2003.Cancer Gene Therapy 10: 737-744.*

* cited by examiner

*Primary Examiner* — Padmavathi Baskar
(74) *Attorney, Agent, or Firm* — Tully Rinckey PLLC; Steven M. Hoffberg

(57) ABSTRACT

Bacterial strains are provided having at least one of a reduced size, a sialic acid coat, inducibly altered surface antigens, and expression of PD-L1 or CTLA-4 agonists and/or tryptophanase. The bacteria may have improved serum half-life, increased penetration into tumors, increased tumor targeting and increased antitumor activity. The bacteria are useful for delivery of therapeutic agents that treat of neoplastic diseases including solid tumors and lymphomas.

15 Claims, 4 Drawing Sheets
Specification includes a Sequence Listing.

SEQUENCE LISTING

```
<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Chlamydia specific histone-like protein binding
      sequence 1

<400> SEQUENCE: 1
aatagggttt cttttaatag aaac                                            24

<210> SEQ ID NO 2
<211> LENGTH: 24
<212> TYPE: DNA
<213> ORGANISM: Artificial Sequence
<220> FEATURE:
<223> OTHER INFORMATION: Chlamydia specific histone-like protein binding
      sequence 2

<400> SEQUENCE: 2
aatagggatt ccagtaacaa caag                                            24

<210> SEQ ID NO 3
<211> LENGTH: 1053
<212> TYPE: DNA
<213> ORGANISM: Artificial Sequence
<220> FEATURE:
```

<223> OTHER INFORMATION: upstream regulon promoter/operator, MarR and
      MarA genes, start codon (ATG) fusion

<400> SEQUENCE: 3

```
cagtgtgcaa gttaatatcc tctacaacct ataacctgta attatcaatt agttacaagt     60
tatcacagca aatacccccg gacgcctttt agcaaatcgt ggcatcggcc aattcattta    120
gttgacttat acttgcctgg gcaatagtat ctgacgaaat taattacttg ccggggcaac    180
cattttgaaa agcaccagtg atctgttcaa tgaaatcatt ccgctgggtc gcttgatcta    240
catggtaaat cagaaaaaag atcgcctgtt aaataactat ttatccccgc tggatatcac    300
cgcaacacag tttaaagtgc tttgctcgat acgctgcgcg ggatgtatta ccccggttga    360
acttaaaaaa gtgctgtctg tcgatctcgg cgcattgacg cggatgctcg accgcctgct    420
gtgcaaaggc tggatcgaaa gactgccgaa tcctaatgac aaacgcggcg tactggtgaa    480
gctaacgccg gacggcgcgg caatttgtga gcaatgtcat caacgaccag gcaagacct    540
gcatcaggaa ttaacaaaaa acttaacggc ggacgaagtg gcaacgcttg agtatttgct    600
caagaaaatt ctgccgtaga caaaaagag gtatgacgat gtccagacgc aacactgacg    660
ctattactat tcatagcatt ttggactgga tcgaggataa cctggagtcg ccgctctcac    720
tggaaaaagt gtctgagcgt tcaggatatt ccaaatggca cctgcaacgg atgtttaaaa    780
aagagaccgg tcattcatta ggccaataca tccgcagccg taaaatgacg gaaatcgcgc    840
aaaaattaaa agagagcaac gagcccattc tctatctggc ggaacgctat ggctttgagt    900
cacagcaaac attgacccgg acgttcaaaa actatttga tgtgccgcca cacaaatacc    960
ggatcaccaa tatgcatggc gaatcacggt atatgctgcc gctgaaccat ggcaactact   1020
agtttgttta tgcgccacgc gaagagcacc atg                                1053
```

<210> SEQ ID NO 4
<211> LENGTH: 24
<212> TYPE: PRT
<213> ORGANISM: Escherichia coli

<400> SEQUENCE: 4

```
Met Asn Ile Leu His Ile Cys Val Thr Ser Lys Trp Phe Asn Ile Asp
1               5                   10                  15

Asn Lys Ile Val Asp His Arg Pro
            20
```

<210> SEQ ID NO 5
<211> LENGTH: 471
<212> TYPE: PRT
<213> ORGANISM: Escherichia coli

<400> SEQUENCE: 5

```
Met Glu Asn Phe Lys His Leu Pro Glu Pro Phe Arg Ile Arg Val Ile
1               5                   10                  15

Glu Pro Val Lys Arg Thr Thr Arg Ala Tyr Arg Glu Glu Ala Ile Ile
            20                  25                  30

Lys Ser Gly Met Asn Pro Phe Leu Leu Asp Ser Glu Asp Val Phe Ile
        35                  40                  45

Asp Leu Leu Thr Asp Ser Gly Thr Gly Ala Val Thr Gln Ser Met Gln
    50                  55                  60

Ala Ala Met Met Arg Gly Asp Glu Ala Tyr Ser Gly Ser Arg Ser Tyr
65                  70                  75                  80

Tyr Ala Leu Ala Glu Ser Val Lys Asn Ile Phe Gly Tyr Gln Tyr Thr
```

```
                  85                  90                  95
Ile Pro Thr His Gln Gly Arg Gly Ala Glu Gln Ile Tyr Ile Pro Val
            100                 105                 110
Leu Ile Lys Lys Arg Glu Gln Glu Lys Gly Leu Asp Arg Ser Lys Met
        115                 120                 125
Val Ala Phe Ser Asn Tyr Phe Asp Thr Thr Gln Gly His Ser Gln
    130                 135                 140
Ile Asn Gly Cys Thr Val Arg Asn Val Tyr Ile Lys Glu Ala Phe Asp
145                 150                 155                 160
Thr Gly Val Arg Tyr Asp Phe Lys Gly Asn Phe Asp Leu Glu Gly Leu
                165                 170                 175
Glu Arg Gly Ile Glu Glu Val Gly Pro Asn Asn Val Pro Tyr Ile Val
            180                 185                 190
Ala Thr Ile Thr Ser Asn Ser Ala Gly Gly Gln Pro Val Ser Leu Ala
        195                 200                 205
Asn Leu Lys Ala Met Tyr Ser Ile Ala Lys Lys Tyr Asp Ile Pro Val
    210                 215                 220
Val Met Asp Ser Ala Arg Phe Ala Glu Asn Ala Tyr Phe Ile Lys Gln
225                 230                 235                 240
Arg Glu Ala Glu Tyr Lys Asp Trp Thr Ile Glu Gln Ile Thr Arg Glu
                245                 250                 255
Thr Tyr Lys Tyr Ala Asp Met Leu Ala Met Ser Ala Lys Lys Asp Ala
            260                 265                 270
Met Val Pro Met Gly Gly Leu Leu Cys Met Lys Asp Asp Ser Phe Phe
        275                 280                 285
Asp Val Tyr Thr Glu Cys Arg Thr Leu Cys Val Val Gln Glu Gly Phe
    290                 295                 300
Pro Thr Tyr Gly Gly Leu Glu Gly Gly Ala Met Glu Arg Leu Ala Val
305                 310                 315                 320
Gly Leu Tyr Asp Gly Met Asn Leu Asp Trp Leu Ala Tyr Arg Ile Ala
                325                 330                 335
Gln Val Gln Tyr Leu Val Asp Gly Leu Glu Glu Ile Gly Val Val Cys
            340                 345                 350
Gln Gln Ala Gly Gly His Ala Ala Phe Val Asp Ala Gly Lys Leu Leu
        355                 360                 365
Pro His Ile Pro Ala Asp Gln Phe Pro Ala Gln Ala Leu Ala Cys Glu
    370                 375                 380
Leu Tyr Lys Val Ala Gly Ile Arg Ala Val Glu Ile Gly Ser Phe Leu
385                 390                 395                 400
Leu Gly Arg Asp Pro Lys Thr Gly Lys Gln Leu Pro Cys Pro Ala Glu
                405                 410                 415
Leu Leu Arg Leu Thr Ile Pro Arg Ala Thr Tyr Thr Gln Thr His Met
            420                 425                 430
Asp Phe Ile Ile Glu Ala Phe Lys His Val Lys Glu Asn Ala Ala Asn
        435                 440                 445
Ile Lys Gly Leu Thr Phe Thr Tyr Glu Pro Lys Val Leu Arg His Phe
    450                 455                 460
Thr Ala Lys Leu Lys Glu Val
465                 470

<210> SEQ ID NO 6
<211> LENGTH: 415
<212> TYPE: PRT
<213> ORGANISM: Escherichia coli
```

<400> SEQUENCE: 6

```
Met Thr Asp Gln Ala Glu Lys Lys His Ser Ala Phe Trp Gly Val Met
1               5                   10                  15

Val Ile Ala Gly Thr Val Ile Gly Gly Met Phe Ala Leu Pro Val
            20                  25                  30

Asp Leu Ala Gly Ala Trp Phe Phe Trp Gly Ala Phe Ile Leu Ile Ile
            35                  40                  45

Ala Trp Phe Ser Met Leu His Ser Gly Leu Leu Leu Glu Ala Asn
50                  55                  60

Leu Asn Tyr Pro Val Gly Ser Ser Phe Asn Thr Ile Thr Lys Asp Leu
65                  70                  75                  80

Ile Gly Asn Thr Trp Asn Ile Ile Ser Gly Ile Thr Val Ala Phe Val
                85                  90                  95

Leu Tyr Ile Leu Thr Tyr Ala Tyr Ile Ser Ala Asn Gly Ala Ile Ile
                100                 105                 110

Ser Glu Thr Ile Ser Met Asn Leu Gly Tyr His Ala Asn Pro Arg Ile
            115                 120                 125

Val Gly Ile Cys Thr Ala Ile Phe Val Ala Ser Val Leu Trp Leu Ser
            130                 135                 140

Ser Leu Ala Ala Ser Arg Ile Thr Ser Leu Phe Leu Gly Leu Lys Ile
145                 150                 155                 160

Ile Ser Phe Val Ile Val Phe Gly Ser Phe Phe Gln Val Asp Tyr
                165                 170                 175

Ser Ile Leu Arg Asp Ala Thr Ser Ser Thr Ala Gly Thr Ser Tyr Phe
                180                 185                 190

Pro Tyr Ile Phe Met Ala Leu Pro Val Cys Leu Ala Ser Phe Gly Phe
            195                 200                 205

His Gly Asn Ile Pro Ser Leu Ile Ile Cys Tyr Gly Lys Arg Lys Asp
            210                 215                 220

Lys Leu Ile Lys Ser Val Val Phe Gly Ser Leu Ala Leu Val Ile
225                 230                 235                 240

Tyr Leu Phe Trp Leu Tyr Cys Thr Met Gly Asn Ile Pro Arg Glu Ser
                245                 250                 255

Phe Lys Ala Ile Ile Ser Ser Gly Gly Asn Val Asp Ser Leu Val Lys
            260                 265                 270

Ser Phe Leu Gly Thr Lys Gln His Gly Ile Ile Glu Phe Cys Leu Leu
            275                 280                 285

Val Phe Ser Asn Leu Ala Val Ala Ser Ser Phe Gly Val Thr Leu
290                 295                 300

Gly Leu Phe Asp Tyr Leu Ala Asp Leu Phe Lys Ile Asp Asn Ser His
305                 310                 315                 320

Gly Gly Arg Phe Lys Thr Val Leu Leu Thr Phe Leu Pro Pro Ala Leu
                325                 330                 335

Leu Tyr Leu Ile Phe Pro Asn Gly Phe Ile Tyr Gly Ile Gly Gly Ala
                340                 345                 350

Gly Leu Cys Ala Thr Ile Trp Ala Val Ile Pro Ala Val Leu Ala
            355                 360                 365

Ile Lys Ala Arg Lys Lys Phe Pro Asn Gln Met Phe Thr Val Trp Gly
            370                 375                 380

Gly Asn Leu Ile Pro Ala Ile Val Ile Leu Phe Gly Ile Thr Val Ile
385                 390                 395                 400

Leu Cys Trp Phe Gly Asn Val Phe Asn Val Leu Pro Lys Phe Gly
```

<210> SEQ ID NO 7
<211> LENGTH: 3049
<212> TYPE: DNA
<213> ORGANISM: Escherichia coli

<400> SEQUENCE: 7

| | | | | | |
|---|---|---|---|---|---|
| atgaatatct | tacatatatg | tgtgacctca | aaatggttca | atattgacaa | caaaattgtc | 60 |
| gatcaccgcc | cttgatttgc | ccttctgtag | ccatcaccag | agccaaaccg | attagattca | 120 |
| atgtgatcta | tttgtttgct | atatcttaat | tttgccttt | gcaaaggtca | tctctcgttt | 180 |
| atttacttgt | tttagtaaat | gatggtgctt | gcatatatat | ctggcgaatt | aatcggtata | 240 |
| gcagatgtaa | tattcacagg | gatcactgta | attaaaataa | atgaaggatt | atgtaatgga | 300 |
| aaactttaaa | catctccctg | aaccgttccg | cattcgtgtt | attgagccag | taaaacgtac | 360 |
| cactcgcgct | tatcgtgaag | aggcaattat | taaatccggt | atgaacccgt | tcctgctgga | 420 |
| tagcgaagat | gtttttatcg | atttactgac | cgacagcggc | accggggcgg | tgacgcagag | 480 |
| catgcaggct | gcgatgatgc | gcggcgacga | agcctacagc | ggcagtcgta | gctactatgc | 540 |
| gttagccgag | tcagtgaaaa | atatctttgg | ttatcaatac | accattccga | ctcaccaggg | 600 |
| ccgtggcgca | gagcaaatct | atattccggt | actgattaaa | aaacgcgagc | aggaaaaagg | 660 |
| cctggatcgc | agcaaaatgg | tggcgttctc | taactatttc | tttgatacca | cgcagggcca | 720 |
| tagccagatc | aacggctgta | ccgtgcgtaa | cgtctatatc | aaagaagcct | tcgatacggg | 780 |
| cgtgcgttac | gactttaaag | caactttga | ccttgaggga | ttagaacgcg | gtattgaaga | 840 |
| agttggtccg | aataacgtgc | cgtatatcgt | tgcaaccatc | accagtaact | ctgcaggtgg | 900 |
| tcagccggtt | tcactggcaa | acttaaaagc | gatgtacagc | atcgcgaaga | aatacgatat | 960 |
| tccggtggta | atggactccg | cgcgctttgc | tgaaaacgcc | tatttcatca | gcagcgtga | 1020 |
| agcagaatac | aaagactgga | ccatcgagca | gatcaccgc | gaaacctaca | aatatgccga | 1080 |
| tatgctggcg | atgtccgcca | agaaagatgc | gatggtgccg | atgggcggcc | tgctgtgcat | 1140 |
| gaaagacgac | agcttctttg | atgtgtacac | cgagtgcaga | acccttgcg | tggtgcagga | 1200 |
| aggcttcccg | acatatggcg | gcctggaagg | cggcgcgatg | gagcgtctgg | cggtaggtct | 1260 |
| gtatgacggc | atgaatctcg | actggctggc | ttatcgtatc | gcgcaggtac | agtatctggt | 1320 |
| cgatggtctg | gaagagattg | gcgttgtctg | ccagcaggcg | ggcggtcacg | cggcattcgt | 1380 |
| tgatgccggt | aaactgttgc | cgcatatccc | ggcagaccag | ttcccggcac | aggcgctggc | 1440 |
| ctgcgagctg | tataaagtcg | ccggtatccg | tgcggtagaa | attggctctt | tcctgttagg | 1500 |
| ccgcgatccg | aaaaccggta | acaactgcc | atgcccggct | gaactgctgc | gtttaaccat | 1560 |
| tccgcgcgca | acatatactc | aaacacatat | ggacttcatt | attgaagcct | taaacatgt | 1620 |
| gaaagagaac | gcggcgaata | ttaaaggatt | aaccttacg | tacgaaccga | agtattgcg | 1680 |
| tcacttcacc | gcaaaactta | agaagtttta | attaatacta | cagagtggct | ataaggatgt | 1740 |
| tagccactct | cttaccctac | atcctcaata | acaaaaatag | ccttcctcta | aggtggcat | 1800 |
| catgactgat | caagctgaaa | aaagcactc | tgcatttgg | ggtgttatgg | ttatagcagg | 1860 |
| tacagtaatt | ggtggaggta | tgtttgcttt | acctgttgat | cttgccggtg | cctggttttt | 1920 |
| ctggggtgcc | tttatcctta | tcattgcctg | gttttcaatg | cttcattccg | ggttattgtt | 1980 |
| attagaagca | aatttaaatt | atcccgtcgg | ctccagtttt | aacaccatca | ccaaagattt | 2040 |
| aatcggtaac | acctggaaca | ttatcagcgg | tattaccgtt | gccttcgttc | tctatatcct | 2100 |

| | |
|---|---|
| cacttatgcc tatatctctg ctaatggtgc gatcattagt gaaacgatat caatgaattt | 2160 |
| gggttatcac gctaatccac gtattgtcgg gatctgcaca gccatttcg ttgccagcgt | 2220 |
| attgtggtta agttcgttag ccgccagtcg tattacctca ttgttcctcg ggctgaagat | 2280 |
| tatctccttt gtgatcgtgt ttggttcttt tttcttccag gtcgattact ccattctgcg | 2340 |
| cgacgccacc agctccactg cgggaacgtc ttacttcccg tatatcttta tggctttgcc | 2400 |
| ggtgtgtctg gcgtcatttg gtttccacgg caatattccc agcctgatta tttgctatgg | 2460 |
| aaaacgcaaa gataagttaa tcaaaagcgt ggtatttggt tcgctgctgg cgctggtgat | 2520 |
| ttatctcttc tggctctatt gcaccatggg gaatattccg cgagaaagct taaggcgat | 2580 |
| tatctcctca ggcggcaacg ttgattcgct ggtgaaatcg ttcctcggca ccaaacagca | 2640 |
| cggcattatc gagttttgcc tgctggtgtt ctctaactta gctgttgcca gttcgttctt | 2700 |
| tggtgtcacg ctggggttgt tcgattatct ggcggacctg tttaagattg ataactccca | 2760 |
| cggcgggcgt ttcaaaaccg tgctgttaac cttcctgcca cctgcgttgt tgtatctgat | 2820 |
| cttcccgaac ggctttattt acgggatcgg cggtgccggg ctgtgcgcca ccatctgggc | 2880 |
| ggtcattatt cccgcagtgc ttgcaatcaa agctcgcaag aagtttccca atcagatgtt | 2940 |
| cacggtctgg ggcggcaatc ttattccggc gattgtcatt ctctttggta taaccgtgat | 3000 |
| tttgtgctgg ttcggcaacg tctttaacgt gttacctaaa tttggctaa | 3049 |

<210> SEQ ID NO 8
<211> LENGTH: 60
<212> TYPE: DNA
<213> ORGANISM: Artificial Sequence
<220> FEATURE:
<223> OTHER INFORMATION: Forward primer =Tryp Kpn Nsi F1

<400> SEQUENCE: 8

| | |
|---|---|
| tcggtaccca ggaggaattc accatgcata atatcttaca tatatgtgtg acctcaaaat | 60 |

<210> SEQ ID NO 9
<211> LENGTH: 38
<212> TYPE: DNA
<213> ORGANISM: Artificial Sequence
<220> FEATURE:
<223> OTHER INFORMATION: reverse primer = Tryp Xba R1

<400> SEQUENCE: 9

| | |
|---|---|
| gatctctaga gaaggattta gccaaattta ggtaacac | 38 |

<210> SEQ ID NO 10
<211> LENGTH: 2788
<212> TYPE: DNA
<213> ORGANISM: Artificial Sequence
<220> FEATURE:
<223> OTHER INFORMATION: modified pTrc99a with the arabinose promoter

<400> SEQUENCE: 10

| | |
|---|---|
| gggggcggcc gcaagaaacc aattgtccat attgcatcag acattgccgt cactgcgtct | 60 |
| tttactggct cttctcgcta accaaaccgg taaccccgct tattaaaagc attctgtaac | 120 |
| aaagcgggac caaagccatg acaaaaacgc gtaacaaaag tgtctataat cacggcagaa | 180 |
| aagtccacat tgattatttg cacggcgtca cactttgcta tgccatagca ttttatcca | 240 |
| taagattagc ggatcctacc tgacgctttt tatcgcaact ctctactgtt tctccatacc | 300 |
| cgtttttttg ggctagcgaa ttcgagctcg gtacccagga ggaattcacc atggaattcg | 360 |

```
agctcggtac ccggggatcc tctagagtcg acctgcaggc atgcaagctt ggctgttttg    420
gcggatgaga gaagattttc agcctgatac agattaaatc agaacgcaga agcggtctga    480
taaaacagaa tttgcctggc ggcagtagcg cggtggtccc acctgacccc atgccgaact    540
cagaagtgaa acgccgtagc gccgatggta gtgtggggtc tccccatgcg agagtaggga    600
actgccaggc atcaaataaa acgaaaggct cagtcgaaag actgggcctt tcgttttatc    660
tgttgtttgt cggtgaacgc tctcctgagt aggacaaatc cgccgggagc ggatttgaac    720
gttgcgaagc aacggcccgg agggtggcgg gcaggacgcc cgccataaac tgccaggcat    780
caaattaagc agaaggccat cctgacggat ggcctttttg cgtttctaca aactcttttt    840
gtttattttt ctaaatacat tcaaatatgt atccgctcat gagacaataa ccctgataaa    900
tgcttcaata atattgaaaa aggaagagta tgagtattca acatttccgt gtcgccctta    960
ttcccttttt tgcggcattt tgccttcctg ttttgctca cccagaaacg ctggtgaaag    1020
taaaagatgc tgaagatcag ttgggtgcac gagtgggtta catcgaactg gatctcaaca    1080
gcggtaagat ccttgagagt tttcgccccg aagaacgttt tccaatgatg agcactttta    1140
aagttctgct atgtggcgcg gtattatccc gtgttgacgc cgggcaagag caactcggtc    1200
gccgcataca ctattctcag aatgacttgg ttgagtactc accagtcaca gaaaagcatc    1260
ttacggatgg catgacagta agagaattat gcagtgctgc cataaccatg agtgataaca    1320
ctgcggccaa cttacttctg acaacgatcg gaggaccgaa ggagctaacc gcttttttgc    1380
acaacatggg ggatcatgta actcgccttg atcgttggga accggagctg aatgaagcca    1440
taccaaacga cgagcgtgac accacgatgc ctacagcaat ggcaacaacg ttgcgcaaac    1500
tattaactgg cgaactactt actctagctt cccggcaaca attaatagac tggatggagg    1560
cggataaagt tgcaggacca cttctgcgct cggcccttcc ggctggctgg tttattgctg    1620
ataaatctgg agccggtgag cgtgggtctc gcggtatcat tgcagcactg gggccagatg    1680
gtaagccctc ccgtatcgta gttatctaca cgacggggag tcaggcaact atggatgaac    1740
gaaatagaca gatcgctgag ataggtgcct cactgattaa gcattggtaa ctgtcagacc    1800
aagtttactc atatatactt tagattgatt taaaacttca ttttaatttt aaaaggatct    1860
aggtgaagat cctttttgat aatctcatga ccaaaatccc ttaacgtgag ttttcgttcc    1920
actgagcgtc agaccccgta gaaaagatca aaggatcttc ttgagatcct ttttttctgc    1980
gcgtaatctg ctgcttgcaa acaaaaaaac caccgctacc agcggtggtt tgtttgccgg    2040
atcaagagct accaactctt tttccgaagg taactggctt cagcagagcg cagataccaa    2100
atactgtcct tctagtgtag ccgtagttag gccaccactt caagaactct gtagcaccgc    2160
ctacatacct cgctctgcta atcctgttac cagtggctgc tgccagtggc gataagtcgt    2220
gtcttaccgg gttggactca agacgatagt taccggataa ggcgcagcgg tcgggctgaa    2280
cggggggttc gtgcacacag cccagcttgg agcgaacgac ctacaccgaa ctgagatacc    2340
tacagcgtga gctatgagaa agcgccacgc ttcccgaagg gagaaaggcg gacaggtatc    2400
cggtaagcgg cagggtcgga acaggagagc gcacagggga gcttccaggg ggaaacgcct    2460
ggtatcttta tagtcctgtc gggtttcgcc acctctgact tgagcgtcga ttttgtgat    2520
```

```
                                           -continued gctcgtcagg ggggcggagc ctatggaaaa acgccagcaa cgcggccttt ttacggttcc    2580
tggccttttg ctggccttttt gctcacatgt tctttcctgc gttatcccct gattctgtgg    2640
ataaccgtat taccgccttt gagtgagctg ataccgctcg ccgcagccga acgaccgagc    2700
gcagcgagtc agtgagcgag gaagcggaag agcgcctgat gcggtatttt ctccttacgc    2760
atctgtgcgg tatttcacac cgcatatg                                       2788
```

MODIFIED BACTERIA HAVING IMPROVED PHARMACOKINETICS AND TUMOR COLONIZATION ENHANCING ANTITUMOR ACTIVITY

CROSS REFERENCE TO RELATED APPLICATIONS

The present application is Divisional of U.S. patent application Ser. No. 14/858,810, filed Sep. 18, 2015, now U.S. Pat. No. 9,616,114, issued Apr. 11, 2017, which is a nonprovisional of, and claims benefit of priority under 35 U.S.C. § 119(e) from, U.S. Provisional Patent Application No. 62/052,252, filed Sep. 18, 2014, the entirety of which is expressly incorporated herein by reference.

1. FIELD OF THE INVENTION

This invention is generally in the field of therapeutic delivery systems utilizing live bacteria for the diagnosis and treatment of neoplastic disease.

2. BACKGROUND OF THE INVENTION

Citation or identification of any reference herein, or any section of this application shall not be construed as an admission that such reference is available as prior art to the present application. The disclosures of each of these publications and patents are hereby incorporated by reference in their entirety in this application, and shall be treated as if the entirety thereof forms a part of this application. Such references are provided for their disclosure of technologies to enable practice of the present invention, to provide basis for claim language, to make clear applicant's possession of the invention with respect to the various aggregates, combinations, and subcombinations of the respective disclosures or portions thereof (within a particular reference or across multiple references). The citation of references is intended to be part of the disclosure of the invention, and not merely supplementary background information. The incorporation by reference does not extend to teachings which are inconsistent with the invention as expressly described herein, and is evidence of a proper interpretation by persons of ordinary skill in the art of the terms, phrase and concepts discussed herein, without being limiting as the sole interpretation available.

Cancer or neoplastic diseases including solid tumors, lymphomas, leukemias or leukemic bone marrow, is a devastating condition of uncontrolled cell growth, which often has the ability to spread throughout the body (metastases) resulting in death. Tumor-targeted bacteria offer tremendous potential advantages for the treatment of solid tumors, including the targeting from a distant inoculation site and the ability to express therapeutic agents directly within the tumor (Pawelek et al., 1997, Tumor-targeted *Salmonella* as a novel anticancer agent, Cancer Research 57: 4537-4544; Low et al., 1999, Lipid A mutant *salmonella* with suppressed virulence and TNF-alpha induction retain tumor-targeting in vivo, Nature Biotechnol. 17: 37-41), each of which is expressly incorporated herein by reference in its entirety.

The primary shortcoming of tumor-targeted bacteria investigated in the human clinical trials (*Salmonella* strain VNP20009 and its derivative TAPET-CD; Toso et al., 2002, Phase I study of the intravenous administration of attenuated *Salmonella typhimurium* to patients with metastatic melanoma, J. Clin, Oncol. 20: 142-152; Meir et al., 2001, Phase 1 trial of a live, attenuated *Salmonella Typhimurium* (VNP20009) administered by direct Intra-tumoral (IT) injection, Proc Am Soc Clin Oncol 20: abstr 1043); Nemunaitis et al., 2003, Pilot trial of genetically modified, attenuated *Salmonella* expressing the *E. coli* cytosine deaminase gene in refractory cancer patients, Cancer Gene Therapy 10: 737-744, each of which is expressly incorporated herein by reference in its entirety) was that no significant antitumor activity was observed, even in patients where the bacteria was documented to target the tumor. In addition, an important factor was also that bacterial colonization of tumors, both in the form of the percentage of tumors that were colonized and amount of the bacteria that accumulated within the tumors, was usually lower compared to the preclinical studies using mice. One method of increasing the ability of the bacteria to expand their numbers within tumors is to kill tumor cells by engineering the bacteria to express conventional bacterial toxins (e.g., WO2009/126189, WO03/014380, WO/2005/018332, WO/2008/073148, US 2003/0059400 U.S. Pat. Nos. 7,452,531, 7,354,592, 6,962, 696, 6,923,972, 6,863,894, 6,685,935, 6,475,482, 6,447,784, 6,190,657 and 6,080,849, each of which is expressly incorporated herein by reference in its entirety).

Use of secreted proteins in live bacterial vectors has been demonstrated by several authors. Holland et al. (U.S. Pat. No. 5,143,830, expressly incorporated in its entirety herein by reference in its entirety) have illustrated the use of fusions with the C-terminal portion of the hemolysin A (hlyA) gene, a member of the type I secretion system. When co-expressed in the presence of the hemolysin protein secretion channel (hlyBD) and a functional TolC, heterologous fusions are readily secreted from the bacteria. The type I secretion system that has been utilized most widely, and although it is currently considered the best system available, is thought to have limitations for delivery by attenuated bacteria (Hahn and Specht, 2003, FEMS Immunology and Medical Microbiology, 37: 87-98, expressly incorporated herein by reference in its entirety). Those limitations include the amount of protein secreted and the ability of the protein fused to it to interfere with secretion. Improvements of the type I secretion system have been demonstrated by Sugamata and Shiba (2005 Applied and Environmental Micobiology 71: 656-662), expressly incorporated herein by reference in its entirety, using a modified hlyB, and by Gupta and Lee (2008 Biotechnology and Bioengineering, 101: 967-974), expressly incorporated herein by reference in its entirety, by addition of rare codons to the hlyA gene, each of which is expressly incorporated by reference in their entirety herein. Fusion to the gene ClyA (Galen et al., 2004, Infection and Immunity, 72: 7096-7106 and Type III secretion proteins have also been used. Surface display has been used to export proteins outside of the bacteria. For example, fusion of the Lpp protein amino acids 1-9 with the transmembrane region B3-B7 of OmpA has been used for surface display (Samuelson et al., 2002, Display of proteins on bacteria, J. Biotechnology 96: 129-154, expressly incorporated by reference in its entirety). The autotransporter surface display has been described by Berthet et al., WO/2002/070645, expressly incorporated by reference in its entirety. Other heterologous protein secretion systems utilizing the autotransporter family can be modulated to result in either surface display or complete release into the medium (see Henderson et al., 2004, Type V secretion pathway: the autotransporter story, Microbiology and Molecular Biology Reviews 68: 692-744; Jose, 2006 Applied Microbiol. Biotechnol. 69: 607-614; Jose J, Zangen D (2005) Autodisplay of the protease inhibitor aprotinin in *Escherichia coli*. Biochem Biophys Res Commun 333:1218-1226 and Rutherford and Mourez 2006 Microbial Cell Factories 5: 22). For example, Veiga et al. (2003 Journal of Bacteriology 185: 5585-5590 and Klauser et al., 1990 EMBO Journal 9: 1991-1999), each of which is expressly incorporated herein by reference in its entirety, demonstrated hybrid proteins containing the b-autotransporter domain of the immunoglobulin A (IgA) protease of Nisseria gonorrhea. Fusions to flagellar proteins have been demonstrated. The peptide, usually of 15 to 36 amino acids in length, is inserted into the central, hypervariable region of the FliC gene such as that from Salmonella muenchen (Verma et al. 1995 Vaccine 13: 235-24; Wu et al., 1989 Proc. Natl. Acad. Sci. USA 86: 4726-4730; Cuadro et al., 2004 Infect. Immun. 72: 2810-2816; Newton et al., 1995, Res. Microbiol. 146: 203-216, each of which is expressly incorporated by reference in its entirety). Multihybrid FliC insertions of up to 302 amino acids have also been prepared (Tanskanen et al. 2000, Appl. Env. Microbiol. 66: 4152-4156, each of which is expressly incorporated by reference in its entirety). Trimerization of antigens and functional proteins can be achieved using the T4 fibritin foldon trimerization sequence (Wei et al. 2008 J. Virology 82: 6200-6208) and VASP tetramerization domains (Kühnel et al., 2004 PNAS 101: 17027-17032), each of which is expressly incorporated by reference in its entirety. The multimerization domains are used to create, bi-specific, tri-specific, and quatra-specific targeting agents, whereby each individual agent is expressed with a multimerization tag, each of which may have the same or separate targeting peptide, such that following expression, surface display, secretion and/or release, they form multimers with multiple targeting domains. Other secretion systems include C-terminal fusions to the protein YebF (Zhang et al., 2006, Extracellular accumulation of recombinant proteins fused to the carrier protein YebF in Escherichia coli, Nat Biotechnol 24: 100-104, expressly incorporated herein by reference in its entirety), which is commercially available as a kit (pAES40; AthenaES, Baltimore, Md.). Fusions to OmsY and other proteins are also capable of secreting proteins into the medium (Zian et al., 2008, Proteome-Based Identification of Fusion Partner for High-Level Extracellular Production of Recombinant Proteins in Escherichia coli, Biotechnol Bioengineer 101: 587-601), expressly incorporated herein by reference in its entirety. Other secretions systems usable according to the present invention include that of Kotzsch et al. 2011 (A secretory system for bacterial production of high-profile protein targets, Protein Science 20: 597-609) using OmpA, OmpF and OsmY, or those described by Yoon et al., 2010 (Secretory production of recombinant proteins in Escherichia coli, Recent Patents on Biotechnology 4: 23-29; US20067094579B2, WO2009021548A1, EP1402036B1, US20067070989B2, US20080193974A1, US20067052867B2, US20036605697B1, U.S. Pat. No. 5,470,719A, US20070287171A1, US20090011995A1, US20080076157A1, US20067112434B2, US20056919198B1, US20026455279B1, US20077291325B2, US20087410788B2, US006083715A, EP1270730A1, US20046673569B1, US016309861B1, U.S. Pat. No. 5,989,868A, US20067056732B2, US20056852512B2, US20056861403B2, EP1407052B1, WO2008089132A2, U.S. Pat. No. 5,824,502A, EP1068339B1, US20080166757A1, US016329172B1, US036596509B1, US20036642027B2, WO2006017929A1, US20036596510B1, US20080280346A1, US20077202059B2, US20080280346A1, US20077202059B2, US20097491528B2, US20080206814A1, US20080166764A1, US20080182295A1, US20080254511A1, US20080206818A1, US20067105327B1, US20040005695A1, U.S. Pat. No. 5,508,192A, EP866132A2, U.S. Pat. No. 6,921,659B2, U.S. Pat. No. 6,828,121B2, US20080064062A1, EP786009B1, US20060270043A1), and Habermann and Ertl (U.S. Pat. No. 7,202,059 Fusion proteins capable of being secreted into a fermentation medium), which uses fusions to hirudin, each of which is expressly incorporated herein by reference in its entirety.

Compositions described in accordance with various embodiments herein include, without limitation, Salmonella enterica serovar Typhimurium ("S. typhimurium"), Salmonella montevideo, Salmonella enterica serovar Typhi ("S. typhi"), Salmonella enterica serovar Paratyphi A, Paratyphi B ("S. paratyphi 13"), Salmonella enterica serovar Paratyphi C ("S. paratyphi C"), Salmonella enterica serovar Hadar ("S. hadar"), Salmonella enterica serovar Enteriditis ("S. enteriditis"), Salmonella enterica serovar Kentucky ("S. kentucky"), Salmonella enterica serovar Infantis ("S. infantis"), Salmonella enterica serovar Pullorum ("S. pullorum"), Salmonella enterica serovar Gallinarum ("S. gallinarum"), Salmonella enterica serovar Muenchen ("S. muenchen"), Salmonella enterica serovar Anaturn ("S. anatum"), Salmonella enterica serovar Dublin ("S. dublin"), Salmonella enterica serovar Derby ("S. derby"), Salmonella enterica serovar Choleraesuis var. kunzendorf ("S. cholerae kunzendorf"), and Salmonella enterica serovar minnesota (S. minnesota). A preferred serotype for the treatment of bone marrow related diseases is S. dublin.

By way of example, live bacteria in accordance with aspects of the invention include known strains of S. enterica serovar Typhimurium (S. typhimurium) and S. enterica serovar Typhi (S. typhi) which are further modified as provided by various embodiments of the invention. Such Strains include Ty21a, CMV906, CMV908, CMV906-htr, CMV908-htr, Ty800, aroA-/serC-, holavax, M01ZH09, VNP20009. See also, U.S. Pat. No. 6,548,287, and EP 0,973,911, each of which is expressly incorporated herein by reference in its entirety. See also, US 20140256922; 20120108640; 20110318308; 20090215754; 20090169517; 20070298012; 20070110752; 20070004666; 20060115483; 20060104955; 20060089350; 20060025387; 20050267103; 20050249706; 20050112642; 20050009750; 20040229338; 20040219169; 20040058849; 20030143676; 20030113293; 20030031628; 20030022835; 20020151063; 20140220661; 20140212396; 20140186401; 20140178341; 20140155343; 20140093885; 20130330824; 20130295054; 20130209405; 20130130292; 20120164687; 20120142080; 20120128594; 20120093773; 20120020883; 20110275585; 20110111496; 20110111481; 20100239546; 20100189691; 20100136048; 20100135973; 20100135961; 20100092438; 20090300779; 20090180955; 20090175829; 20090123426; 20090053186; 20080311081; 20080124355; 20080038296; 20070110721; 20070104689; 20060083716; 20050026866; 20050008618; 20040202663; 20050255088; 20030109026; 20020026655; 20110223241; 20070009489; 20050036987; 20030170276; 20140148582; 20130345114; 20130287810; 20130164380; 20130164307; 20130078275; 20120225454; 20120177682; 20120148601; 20120144509; 20120083587; 20120021517; 20110274719; 20110268661; 20110165680; 20110091493; 20110027349; 20100172976; 20090317404; 20090220540; 20090123382; 20090117049; 20090117048; 20090117047; 20090068226; 20080249013; 20080206284; 20070202591; 20070191262; 20070134264; 20060127408; 20060057152; 20050118193; 20050069491; 20050064526; 20040234455; 20040202648; 20040054142; 20030170211; 20030059400;

20030036644; 20030009015; 20030008839; 20020176848; 20020102242; 20140205538; 20140112951; 20140086950; 20120244621; 20120189572; 20110104196; 20100233195; 20090208534; 20090136542; 20090028890; 20080260769; 20080187520; 20070031382; 20060140975; 20050214318; 20050214317; 20050112140; 20050112139; 20040266003; 20040115174; 20040009936; 20030153527; 20030125278; 20030045492; 8828681; 8822194; 8784836; 8771669; 8734779; 8722668; 8715641; 8703153; 8685939; 8663634; 8647642; 8642257; 8623350; 8604178; 8591862; 8586022; 8568707; 8551471; 8524220; 8440207; 8357486; 8343509; 8323959; 8282919; 8241623; 8221769; 8198430; 8137904; 8066987; 8021662; 8008283; 7998461; 7955600; 7939319; 7915218; 7887816; 7842290; 7820184; 7803531; 7790177; 7786288; 7763420; 7754221; 7740835; 7736898; 7718180; 7700104; 7691383; 7687474; 7662398; 7611883; 7611712; 7588771; 7588767; 7514089; 7470667; 7452531; 7404963; 7393525; 7354592; 7344710; 7247296; 7195757; 7125718; 7084105; 7083791; 7015027; 6962696; 6923972; 6916918; 6863894; 6770632; 6685935; 6682729; 6506550; 6500419; 6475482; 6447784; 6207648; 6190657; 6150170; 6080849; 6030624; and 5877159, each of which is expressly incorporated herein by reference in its entirety.

Novel strains are also encompassed that are, for example, attenuated in virulence by mutations in a variety of metabolic and structural genes. The invention therefore may provide a live composition for treating cancer comprising a live attenuated bacterium that is a serovar of *Salmonella enterica* comprising an attenuating mutation in a genetic locus of the chromosome of said bacterium that attenuates virulence of said bacterium and wherein said attenuating mutation is the Suwwan deletion (Murray et al., 2004. Hot spot for a large deletion in the 18-19 Cs region confers a multiple phenotype in *Salmonella enterica* serovar *Typhimurium* strain ATCC 14028. Journal of Bacteriology 186: 8516-8523 (2004), expressly incorporated herein by reference in its entirety) or combinations with other known attenuating mutations. Other attenuating mutation useful in the *Salmonella* bacterial strains described herein may be in a genetic locus selected from the group consisting of phoP, phoQ, edt, cya, crp, poxA, rpoS, htrA, nuoG, pmi, pabA, pts, damA, pur, purA, purB, purI, purF, zwf, aroA, aroB, aroC, aroD, serC, gua, cadA, rfc, rjb, rfa, ompR, msbB, leucine and arginine, and combinations thereof. Strains of *Salmonella* deleted in stn are particularly preferred.

The invention also encompasses attenuated gram-positive bacteria. For example, *Staphylococcus epidermidis*, group B *Streptococcus* including *S. agalaciae*, and *Listeria* species including *L. monocytogenes* may be employed. It is known to those skilled in the art that variations in molecular biology techniques such as use of gram-positive origins of replication, gram-positive signal sequences and gram-positive promoters and filamentous phage (e.g., phage B5; Chopin et al., 2002 J. Bacteriol. 184: 2030-2033, expressly incorporated herein by reference in its entirety, described further below) may be employed and substituted as needed. Other bacterial strains may also be encompassed, including non-pathogenic bacteria of the gut skin (such as *Staphylococcus epidermidis*, *Proprionibacteria*) and other body locations known as the human microbiome (Grice et al., Topographical and temporal diversity of the human skin microbiome, Science 324: 1190-1192; A framework for human microbiome research; The Human Microbiome Project Consortium, 14 Jun. 2012 Nature 486, 215-221; Spor et al., 2011, Unravelling the effects of the environment and host genotype on the gut microbiome, Nature Reviews Microbiology 9: 279-290, each of which is expressly incorporated herein by reference in its entirety) such as *E. coli* strains, Bacteriodies, *Bifidobacterium* and *Bacillus*, attenuated pathogenic strains of *E. coli* including enteropathogenic and uropathogenic isolates, *Enterococcus* sp. and *Serratia* sp. as well as attenuated *Neisseria* sp., *Shigella* sp., *Staphylococcus* sp., *Staphylococcus carnosis*, *Yersinia* sp., *Streptococcus* sp. and *Listeria* sp. including *L. monocytogenes*. Bacteria of low pathogenic potential to humans and other mammals or birds or wild animals, pets and livestock, such as insect pathogenic *Xenorhabdus* sp., *Photorhabdus* sp. and human wound *Photorhabdus* (*Xenorhabdus*) are also encompassed. Probiotic strains of bacteria are also encompassed, including *Lactobacillus* sp. (e.g., *Lactobacillus acidophilus*, *Lactobacillus salivarius*) *Lactococcus* sp., (e.g., *Lactococcus lactis*, *Lactococcus casei*) *Leuconostoc* sp., *Pediococcus* sp., *Streptococcus* sp. (e.g., *S. salivariu*, *S. thermophilus*), *Bacillus* sp., *Bifidobacterium* sp., *Bacteroides* sp., and *Escherichia coli* such as the 1917 Nissel strain. It is known to those skilled in the art that minor variations in molecular biology techniques such as use of gram-positive origins of replication, gram-positive signal sequences gram-positive promoters (e.g., *Lactococcus* expression, Mohamadzadeh et al., PNAS Mar. 17, 2009 vol. 106 no. 11 4331-4336, expressly incorporated herein by reference in its entirety) may be used and substituted as needed. The bacteria may be further modified to be internalized into the host cell (Guimaraes et al., 2006, Use of Native Lactococci as Vehicles for Delivery of DNA into Mammalian Epithelial Cells, Appl Environ Microbiol. 2006 November; 72(11): 7091-7097; Innocentin et al., 2009, *Lactococcus lactis* Expressing either *Staphylococcus aureus* Fibronectin-Binding Protein A or *Listeria monocytogenes* Internalin A Can Efficiently Internalize and Deliver DNA in Human Epithelial Cells Appl Environ Microbiol. 2009 July; 75(14): 4870-4878, each of which is expressly incorporated herein by reference in its entirety).

The invention also encompasses combinations with known agents, including imatinib and reticuloendothelial system (RES) blocker such as clodronate (dichloromethylene-bisphosphonate; Compositions and methods comprising genetically enhanced obligate and facultative anaerobic bacteria for oncopathic cancer therapy, WO 2009111177, expressly incorporated herein by reference in its entirety) which have the potential to improve the circulation time of the bacteria, vascular permeability inducing agents such as bradykinin, hyperthermia or carbogen which have the potential to improve the permeability of the tumor enhancing entry of the bacteria, or aldose reductase inhibitors.

The invention also encompasses combinations with protease inhibitors and targeted toxins and chimeric toxins and antitumor enzymes and/or genetically engineered phage and phagemids (Bermudes U.S. Pat. No. 8,524,220, Protease Inhibitor: Protease sensitivity expression system composition and methods improving the therapeutic activity and specificity of proteins delivered by bacteria; U.S. Pat. No. 8,241,623, Protease Sensitivity Expression System; U.S. Pat. No. 8,623,350 Protease inhibitor: protease sensitivity expression system and method improving the therapeutic activity and specificity of proteins and phage and phagemids delivered by bacteria, each of which is expressly incorporated herein by reference in its entirety).

The invention also encompasses combinations with antivascular agents, such as platelet factor 4 and thrombospondin, alone or in combination (Bermudes et al., U.S. Pat. No. 6,962,696, U.S. Pat. No. 7,452,531 Compositions and Methods for Tumor-Targeted Delivery of Effector Molecules, each of which is expressly incorporated herein by reference in its entirety).

The present invention provides, according to various embodiments, live attenuated therapeutic bacterial strains that have improved ability compared to a parental strain in regard to the pharmacokinetic properties of enhanced circulation in the bloodstream and entry into, persistence and growth within tumors, by resisting immune elimination or lytic destruction, increased numbers of foci within tumors, increased colonization, expansion and persistence within tumors. It is the intention of these changes that the result in an overall increase in 1) the percentage of tumors targeted, 2) the number of individual locations (foci) within a tumor that are targeted, 3) the number of CFU/g that are found within the tumor, 4) the length of time that they reside within the tumor and 5) reduced immune clearance from the tumor, and, alone or collectively 6) increased antitumor activity.

3. SUMMARY AND OBJECTS OF THE INVENTION

3.1 Improved Pharmacokinetics and Tumor Colonization

The present technology provides compositions and methods to enhance bacterial half-life in the bloodstream, passage out of the vasculature into the target tissue, targeting of tumors and lymphomas, colonization of tumors and lymphomas, expansion within tumor or lymphoma and persistence within tumor and lymphomas, each of which, alone or in combination or subcombination, result in an overall increase in 1) the percentage of tumors and lymphomas targeted, 2) the number of individual locations (foci) within a tumor or lymphoma that are established, 3) the number of colony forming units (CFU/g) that are found within the tumor or lymphoma, 4) the length of time that they reside within the tumor or lymphoma and 5) reduced immune clearance from the tumor or lymphoma, and, alone or collectively, 6) increased anticancer activity.

The compositions or genetically engineered bacteria may comprise at least one of 1) one or more mutations that result in smaller sized bacteria (e.g., smaller volume, smaller surface area, small linear dimensions, or smaller mass) with improved (increased) half-life pharmacokinetics in blood and improved penetration though leaky tumor vasculature, 2) bacteria with a protective sialic acid coat that have improved (increased) pharmacokinetics in blood and improved penetration though leaky tumor vasculature and reduced immune clearance, 3) bacteria that alternately express external antigens such as O and H antigens under exogenous control of inducible promoters such that different antigens are expressed at different times and result in bacteria with improved (increased) pharmacokinetics in blood and reduced immune clearance and reduced immune recognition upon repeated dosing, 4) bacteria that deliver ligands against programmed cell death protein 1 ligand (PD-L1) which sequester or block those ligands and result in T-cells attacking tumors and increasing the habitable region of the tumor by bacteria, 5) expression of the *E. coli* tryptophanase which results in greater tumor cell killing and enhanced penetration of the bacteria within the tumor, and 6) expression of mammalian or bacterial tyrosinase at high (toxic) levels, which e.g., can lead to oxidative stress and metabolic disruption, or prodrug activation.

7) bacteria with resistance to human serum and serum components, which acts as an alternative mechanism to reduced elimination by selection for spontaneously resistant mutants alone or together with $CO_2$ resistance, or expression of serum resistance proteins.

The types of cancers or neoplasias to which the present invention is directed include all neoplastic malignancies, including solid tumors such as those of colon, lung, breast, prostate, sarcomas, carcinomas, head and neck tumors, melanoma, as well as hematological, non-solid or diffuse cancers such as leukemia and lymphomas, myelodysplastic cells, plasma cell myeloma, plasmacytomas, and multiple myelomas. Specific types of cancers include acute lymphoblastic leukemia, acute myeloid leukemia, adrenocortical carcinoma adrenocortical carcinoma, aids-related cancers, aids-related lymphoma, anal cancer, appendix cancer, astrocytomas, childhood, teratoid/rhabdoid tumor, childhood, central nervous system tumors, basal cell carcinoma, bile duct cancer, extrahepatic bladder cancer, bladder cancer, bone cancer, osteosarcoma and malignant fibrous histiocytoma, brain stem glioma, brain tumor, brain stem glioma, central nervous system atypical teratoid/rhabdoid tumor, central nervous system embryonal tumors, brain tumor, astrocytomas, craniopharyngioma, ependymoblastoma, ependymoma, medulloblastoma, medulloepithelioma, pineal parenchymal tumors, supratentorial primitive neuroectodermal tumors and pineoblastoma, spinal cord tumors, breast cancer (female), breast cancer (male), bronchial tumors, burkitt lymphoma, carcinoid tumor, gastrointestinal, nervous system atypical teratoid/rhabdoid tumor, central nervous system embryonal tumors, central nervous system lymphoma, primary cervical cancer, cervical cancer, chordoma, chronic lymphocytic leukemia, chronic myelogenous leukemia, chronic myeloproliferative disorders, colon cancer, colorectal cancer, craniopharyngioma, cutaneous T-cell lymphoma, embryonal tumors, endometrial cancer, ependymoblastoma, ependymoma, esophageal cancer, ewing sarcoma family of tumors, extracranial germ cell tumor, extrahepatic bile duct cancer, eye cancer, intraocular melanoma, eye cancer, retinoblastoma gallbladder cancer, gastric (stomach) cancer, gastrointestinal carcinoid tumor, gastrointestinal stromal tumor (gist), gastrointestinal stromal cell tumor, germ cell tumor, extracranial germ cell tumor, extragonadal germ cell tumor, ovarian gestational trophoblastic tumor, glioma, hairy cell leukemia, head and neck cancer, hepatocellular (liver) cancer, primary hepatocellular (liver) cancer, histiocytosis, langerhans cell, hodgkin lymphoma, hypopharyngeal cancer, intraocular melanoma, islet cell tumors (endocrine pancreas), kaposi sarcoma, kidney (renal cell) cancer, kidney cancer, langerhans cell histiocytosis, laryngeal cancer, leukemia, acute lymphoblastic leukemia, acute myeloid leukemia, chronic lymphocytic leukemia, chronic myelogenous leukemia, hairy cell leukemia, lip and oral cavity cancer, liver cancer, adult (primary) liver cancer, (primary) lung cancer, non-small cell lung cancer, small cell lymphoma, aids-related lymphoma, burkitt lymphoma, cutaneous T-cell lymphoma, hodgkin lymphoma, non-hodgkin lymphoma, primary central nervous system lymphoma, macroglobulinemia, Waldenström malignant fibrous histiocytoma of bone and osteosarcoma, medulloblastoma, melanoma, intraocular (eye) melanoma, merkel cell carcinoma, mesothelioma, metastatic squamous neck cancer with occult primary, mouth cancer, multiple endocrine neoplasia syndrome, childhood multiple myeloma/plasma cell neoplasm, mycosis fungoides, myelodysplastic syndromes, myelodysplastic/myeloproliferative diseases, myelogenous leukemia, chronic myeloid leukemia, adult acute myeloid leukemia, childhood acute myeloma, multiple myeloproliferative disorders, nasal cavity and paranasal sinus cancer, nasopharyngeal cancer, nasopharyngeal cancer, neuroblastoma, non-hodgkin lymphoma, non-small cell lung cancer, oral cancer, oral cavity cancer, lip and oropharyngeal cancer, osteosarcoma and malignant fibrous histiocytoma of bone, ovarian cancer, ovarian epithelial cancer, ovarian germ cell tumor, ovarian low malignant potential tumor, pancreatic cancer, islet cell tumors, papillomatosis, paranasal sinus and nasal cavity cancer, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter, transitional cell cancer, respiratory tract carcinoma involving the nut gene on chromosome 15, retinoblastoma, rhabdomyosarcoma, salivary gland cancer, sarcoma, ewing sarcoma family of tumors, kaposi sarcoma, soft tissue sarcoma, uterine sarcoma, Sézary syndrome, skin cancer (nonmelanoma), melanoma, skin carcinoma, merkel cell, small cell lung cancer, small intestine cancer, soft tissue sarcoma, squamous cell carcinoma, see skin cancer (nonmelanoma), squamous neck cancer with occult primary, metastatic stomach (gastric) cancer, stomach (gastric) cancer, supratentorial primitive neuroectodermal tumors, T-cell lymphoma, cutaneous T-cell lymphoma, mycosis fungoides and Sézary syndrome, testicular cancer, throat cancer, thymoma and thymic carcinoma, thyroid cancer, transitional cell cancer of the renal pelvis and ureter, trophoblastic tumor, (gestational), unknown primary site, carcinoma of, unknown primary site carcinoma, ureter and renal pelvis, transitional cell cancer, urethral cancer, uterine cancer, endometrial uterine sarcoma, vaginal cancer, vulvar cancer, Waldenström macroglobulinemia, and Wilms tumor.

Issues related to bacterial targeting and efficacy have previously been address by Bermudes (Protease sensitivity expression system, U.S. Pat. No. 8,241,623 B1, incorporated by reference in its entirety in this application, and shall be treated as if the entirety thereof forms a part of this application). Survival under $CO_2$ conditions, high osmolarity and acidic conditions has also been addressed (Bermudes U.S. Pat. No. 8,647,642, (Live bacterial vaccines resistant to carbon dioxide (CO2), acidic PH and/or osmolarity for viral infection prophylaxis or treatment), expressly incorporated by reference in its entirety.

As cited above, the primary shortcoming of tumor-targeted bacteria investigated in the human clinical trials (Salmonella strain VNP20009 and its derivative TAPET-CD; Toso et al., 2002, Phase I study of the intravenous administration of attenuated Salmonella typhimurium to patients with metastatic melanoma, J. Clin, Oncol. 20: 142-152; Meir et al., 2001, Phase 1 trial of a live, attenuated Salmonella Typhimurium (VNP20009) administered by direct Intra-tumoral (IT) injection, Proc Am Soc Clin Oncol 20: abstr 1043; Nemunaitis et al., 2003, Pilot trial of genetically modified, attenuated Salmonella expressing the E. coli cytosine deaminase gene in refractory cancer patients, Cancer Gene Therapy 10: 737-744, each of which is expressly incorporated herein by reference in its entirety) is that no antitumor activity was observed, even in patients that were documented to have had tumors that were colonized by the bacteria. An additional divergence between the murine studies (e.g., Pawelek et al., 1997, Tumor-targeted Salmonella as a novel anticancer agent, Cancer Research 57: 4537-4544; Low et al., 1999, Lipid A mutant salmonella with suppressed virulence and TNF-alpha induction retain tumor-targeting in vivo, Nature Biotechnol. 17: 37-41, each of which is expressly incorporated herein by reference in its entirety), is that in most patients, the levels of the bacteria were significantly lower. For example, whereas in the murine models the bacteria frequently achieved levels of $1\times10^9$ colony forming units (CFU) per gram of tumor tissue, in humans the levels were significantly lower, e.g., $1\times10^6$ CFU/g was achieved in 3 patients (Meir et al., 2001). Generally, it has been perceived that the murine studies should precede using bacteria with the greatest amount of tumor targeting. For example, Pawelek et al., WO/1996/040238, expressly incorporated herein by reference in its entirety, selected "super infective" bacteria by cycling through tumors. The novel cycling and selection procedure they employed selected for increased targeting numbers which was correlated with a greater antitumor effect. A similar study using the strain AR-1 was performed by Zhao et al., 2005 (Tumor-targeting bacterial therapy with amino acid auxotrophs of GFP-expressing Salmonella typhimurium) Proc Natl Acad Sci USA. 102: 755-760, expressly incorporated herein by reference in its entirety). In the development of the Salmonella strain A1-R by re-isolation form a tumor, as described by the same group in a later study (Hayashi et al., 2009, Cancer metastasis directly eradicated by targeted therapy with a modified Salmonella typhimurium, Journal of Cellular Biochemistry 106: 992-998, expressly incorporated herein by reference in its entirety) "The idea was to increase the tumor targeting capability of the bacteria." Thus, developing and testing bacteria with enhanced tumor targeting using known genetic backgrounds that already exhibit high levels of tumor targeting has been a focus within the field. However, while it is desirable to find ways to improve the levels of bacteria within tumors, including the present technology, the importance of selecting an appropriate tumor model and/or bacterial genetic background to assess the contribution that an effector system might have in a human, or how it might improve tumor colonization levels, wherein the tumor model and/or bacterial genetic background should provide low (rather than high) levels of tumor colonization, has not been appreciated. It has not been understood that to evaluate how an effector system such as the herpes simplex thymidine kinase or cytosine deaminase described by Pawelek et al., WO/1996/040238, expressly incorporated herein by reference in its entirety, or those provided in the present invention, would function in humans where lower targeting numbers might be expected (at least at the outset; greater number could be achieved if the effector system is effective), such that the murine tumor system and/or bacterial genetic background where the tumor-targeting level is similar to the level achieved in humans represents an appropriate model.

firA is a mutation within the gene that encodes the enzyme UDP-3-O(R-30 hydroxymyristoyl)-glycocyamine N-acyltransferase, that regulates the third step in endotoxin biosynthesis (Kelley et al., 1993, J. Biol. Chem. 268:19866-19874, expressly incorporated herein by reference in its entirety). Salmonella typhimurium and E. coli strains bearing this type of mutation produce a lipid A that differs from wild type lipid A in that it contains a seventh fatty acid, a hexadecanoic acid (Roy and Coleman, 1994, J. Bacteriol. 176:1639-1646, expressly incorporated herein by reference in its entirety). Roy and Coleman demonstrated that in addition to blocking the third step in endotoxin biosynthesis, the firA mutation also decreases enzymatic activity of lipid A 4' kinase that regulates the sixth step of lipid A biosynthesis. Salmonella typhimurium strain SH5014 and its firA' derivative SH7622 are described in Hirvas et al, 1991, EMBO J. 10:1017-1023, expressly incorporated herein by reference in its entirety. The genotypes of these strains are as follows: strain 5115014 ilv-1178 thr-914 ηis-6116 metA22 metE551 trpB2 xyl-404 HI-b H2-e, n, x flaA66 rpsL120 rfaJ4041; strain SH7622 ilv-1178 thr-914 his-6116 metA22 metE551 trpB2 xyl-404 HI-b H2-e, n, x flaββ rpsL120 rfaJ4041, ssc-1 (firA$^{ts}$). A derivative of *Salmonella typhimurium* firA' strain SH7622 was picked, designated SH7622-64, and used as the firA strain for the experiments. SH7622-64 was selected for its supersensitivity to the antibiotic novobiocin and temperature-sensitive growth, characteristics of the firA' SH7622 strain. When studies in two different tumor models, Pawelek et al. found *Salmonella*/g tissue: Primary Tumor of M27 lung cancer, 2.9×10$^6$ per gram and in B16 melanoma, 3.2×10$^5$ per gram, yet retaining a similar 3200:1 tumor to liver targeting ratio. This strain, while never used in any subsequent studies, represents a surprising solution to translating murine to human studies wherein both systems tend to have the same number of bacteria per gram of target tissue.

In an alternative approach to selecting bacterial mutants using strain backgrounds with high tumor-targeting and antitumor effects as is commonly applied (Zhao et al., 2005, Tumor-targeting bacterial therapy with amino acid auxotrophs of GFP-expressing *Salmonella typhimurium*. Proc Natl Acad Sci USA. 102: 755-760, expressly incorporated herein by reference in its entirety), bacterial mutants with suboptimal targeting or low antitumor effects are used for selection of improved antitumor effects. The bacterial mutants can be generated by any standard method of mutation (e.g., UV, nitrosoguanadine, Tn10, Tn5), or can be a spontaneous mutation such as a suppressor mutation (e.g., Murray et al., 2001, Extragenic suppressors of growth defects in msbB *Salmonella*, J. Bacteriol. 183: 5554-5561, expressly incorporated herein by reference in its entirety), or those of the present invention.

Tyrosinase has been proposed as a cancer therapy, e.g., against melanoma. The action may be direct, or by action on a prodrug. See, Claus H, Decker H., Bacterial tyrosinases, Syst Appl Microbiol. 2006 January; 29(1):3-14. Epub 2005 Sep. 6; Maria Simonova, Alexander Wall, Ralph Weissleder, and Alexei Bogdanov, Jr., Tyrosinase Mutants Are Capable of Prodrug Activation in Transfected Nonmelanotic Cells, Cancer Research 60, 6656-6662, Dec. 1, 2000; Connors T. A. The choice of prodrugs for gene directed enzyme prodrug therapy of cancer. Gene Ther., 2: 702-709, 1995; Bridgewater J., Springer C., Knox R., Minton N., Michael N., Collins M. Expression of the bacterial nitroreductase enzyme in mammalian cells renders them selectively sensitive to killing by the prodrug CB1954. Eur. J. Cancer, 31A: 2362-2370, 1995; Austin E., Huber B. A first step in the development of gene therapy for colorectal carcinoma: cloning, sequencing, and expression of *Escherichia coli* cytosine. Mol. Pharmacol., 43: 380-387, 1993; Guzman R., Hirschowitz E., Brody S., Crystal R., Epstein S., Finkel T. In vivo suppression of injury-induced vascular smooth muscle cell accumulation using adenovirus-mediated transfer of the herpes simplex virus thymidine kinase gene. Proc. Natl. Acad. Sci. USA, 91: 10732-10736, 1994; Aghi M., Kramm C., Chou T., Breakefield X., Chiocca E. Synergistic anticancer effects of ganciclovir/thymidine kinase and 5-fluorocytosine/cytosine deaminase gene therapies. J. Natl. Cancer Inst., 90: 370-380, 1998; Jimbow K. Development of targeted chemoradiotherapy for malignant melanoma by exploitation of metabolic pathway. Hokkaido J. Med. Sci., 73: 105-110, 1998; Sterman D., Treat J., Litzky L., Amin K., Coonrod L., Molnar-Kimber K., Recio A., Knox L., Wilson J., Albelda S., Kaiser L. Adenovirus-mediated herpes simplex virus thymidine kinase/ganciclovir gene therapy in patients with localized malignancy: results of a Phase I clinical trial in malignant mesothelioma. Hum. Gene Ther., 9: 1083-1092, 1998; Bakina E., Wu Z., Rosenblum M., Farquhar D. Intensely cytotoxic anthracycline prodrugs: glucuronides. J. Med. Chem., 40: 4013-4018, 1997; Dewey D. L., Butcher F. W., Galpine A. R. Hydroxyanisole-induced regression of the Harding-Passey melanoma in mice. J. Pathol., 122: 117-127, 1977; Wick M. M., Byers L., Ratliff J. Selective toxicity of 6-hydroxydopa for melanoma cells. J. Investig. Dermatol., 72: 67-69, 1979; Jimbow M., Marusyk H., Jimbow K. The in vivo melanocytotoxicity and depigmenting potency of N-2,4-acetoxyphenyl thioethyl acetamide in the skin and hair. Br. J. Dermatol., 133: 526-536, 1995; Jimbow K. N-acetyl-4-S-cysteaminylphenol as a new type of depigmenting agent for the melanoderma of patients with melasma. Arch. Dermatol., 127: 1528-1534, 1991; Singh M. V., Jimbow K. Tyrosinase transfection produces melanin synthesis and growth retardation in glioma cells. Melanoma Res., 8: 493-498, 1998; Toyofuku K., Wada I., Hirosaki K., Park J. S., Hori Y., Jimbow K. Promotion of tyrosinase folding in COS 7 cells by calnexin. J. Biochem. (Tokyo), 125: 82-89, 1999; Sanches-Ferrer A., Rodriguez-Lopez J., Garcia-Canovas F., Garcia-Carnoma F. Tyrosinase: a comprehensive review of its mechanism. Biochim. Biophys. Acta, 1247: 1-11, 1995; Luo D., Chen H., Jimbo K. Cotransfection of genes encoding human tyrosinase and tyrosinase-related protein-1 prevents melanocyte death and enhances melanin pigmentation and gene expression of Lamp-1. Exp. Cell Res., 213: 231-241, 1994; Eberle J., Garbe C., Wang N., Orfanos C. Incomplete expression of the tyrosinase gene family (tyrosinase, TRP-1, and TRP-2) in human malignant melanoma cells in vitro. Pigm. Cell. Res., 8: 307-313, 1995; Riley P. A., Cooksey C. J., Johnson C. I., Land E. J., Latter A. M., Ramsden C. A. Melanogenesis-targeted antimelanoma pro-drug development: effect of side-chain variations on the cytotoxicity of tyrosinase-generated ortho-quinones in a model screening system. Eur. J. Cancer, 33: 135-143, 1997; Bouchard B., Fuller B., Vijayasaraashi S., Houghton A. Induction of pigmentation in mouse fibroblasts by expression of human tyrosinase cDNA. J. Exp. Med., 169: 2029-2042, 1989; Kwon B. S. Pigmentation genes: the tyrosinase gene family and the pmel 17 gene family. J. Investig. Dermatol., 100(Suppl.): 134s-140s, 1993; Beermann F., Orlow S. J., Boissy R. E., Schmidt A., Boissy Y. L., Lamoreux M. L. Misrouting of tyrosinase with a truncated cytoplasmic tail as a result of the murine platinum (cp) mutation. Exp. Eye Res., 61: 599-607, 1995; Chen J., Cha Y., Yuksel K., Gracy R., August J. Isolation and sequencing of a cDNA clone encoding lysosomal membrane glycoprotein mouse LAMP-1. J. Biol. Chem., 263: 8754-8758, 1988; Williams R., Siegle R., Pierce B., Floyd L. Analogs of synthetic melanin polymers for specific imaging applications. Investig. Radiol., 29(Suppl.): 116s-119s, 1994; Kozak M. An analysis of 5'-noncoding sequences from 699 vertebrate messenger RNAs. Nucleic Acids Res., 15: 8125-8148, 1987; Halaban R., Cheng E., Zhang Y., Moellmann G., Hanlon D., Michalak M., Setaluri V., Hebert D. N. Aberrant retention of tyrosinase in the endoplasmic reticulum mediates accelerated degradation of the enzyme and contributes to the dedifferentiated phenotype of amelanotic melanoma cells. Proc. Natl. Acad. Sci. USA, 94: 6210-6215, 1997; Wheeler K., Tel N., Williams M., Sheppard S., Levin V., Kabra P. Factors influencing the survival of rat brain tumor cells after in vitro treatment with 1,3-bis (2-chloroethyl)-1-nitrosourea. Cancer Res., 35: 1464-1469, 1975; Pomerantz S. 1-tyrosine-3,5-3H assay for tyrosinase development in skin of newborn hamsters. Science (Washington D.C.), 164: 838-839, 1969; Mahalingam H., Vaughn J., Novothy J., Gruber J. R., Niles R. M. Regulation of melanogenesis in B16 mouse melanoma cells by protein kinase C. J. Cell. Physiol., 168: 549-558, 1996; Halaban R., Pomerantz S. H., Marshall S., Lambert D. T., Lerner A. B. Regulation of tyrosinase in human melanocytes grown in culture. J. Cell Biol., 97: 480-488, 1983; Enochs W. S., Petherick P., Bogdanova A., Mohr U., Weissleder R. Paramagnetic metal scavenging by melanin: MR imaging. Radiology, 204: 417-423, 1997; Chen Y-T., Stockert E., Tsang S., Coplan K. A., Old L. J. Immunotyping of melanomas for tyrosinase: implications for vaccine development. Proc. Natl. Acad. Sci. USA, 92: 8125-8129, 1995; Padgette S., Herman H., Han J., Pollock S., May S. Antihypertensive activities of phenylaminoethyl sulfides, a class of synthetic substrates for dopamine β-hydroxylase. J. Med. Chem., 27: 5826-5839, 1984; Prezioso J. A., Epperly M. W., Wang N., Bloomer W. D. Effects of tyrosinase activity on the cytotoxicity of 4-S-cysteaminylphenol and N-acetyl-4-S-cysteaminylphenol in melanoma cells. Cancer Lett., 63: 73-79, 1992; Morrison M. E., Yagi M. J., Cohen G. In vitro studies of 2,4-dihydroxyphenylalanine, a prodrug targeted against malignant melanoma cells. Proc. Natl. Acad. Sci. USA, 82: 2960-2964, 1985; Alena F., Jimbo K., Ito S. Melanocytotoxicity and antimelanoma effects of phenolic amine compounds in mice in vivo. Cancer Res., 50: 3743-3747, 1990; Tandon M., Thomas P. D., Shokravi M., Ingh S., Samra S., Chang D., Jimbow K. Synthesis and antimelanoma effect of the melanogenesis-based antimelanoma agent N-propionyl-4-S-cysteaminylphenol. Biochem. Pharmacol., 55: 2023-2029, 1998; Naeyaert J., Eller M., Gordon P., Park H., Gilchrest B. Pigment content of cultured human melanocytes does not correlate with tyrosinase message level. Br. J. Dermatol., 125: 297-303, 1991; Potterf S. B., Muller J., Bernardini I., Tietze F., Kobayashi T., Hearing V. J., Gahl W. A. Characterization of a melanosomal transport system in murine melanocytes mediating entry of the melanogenic substrate tyrosine. J. Biol. Chem., 271: 4002-4008, 1996; Vijayasaradhi S., Bouchard B., Houghton A. N. The melanoma antigen gp 75 is the human homologue of the mouse b (brown) locus gene product. J. Exp. Med., 171: 1375-1380, 1990; Koning G., Morselt H., Velinova M., Donga J., Gorter A., Allen T., Zalipsky S., Kamps J., Scherphof G. Selective transfer of a lipophilic prodrug of 5-fluorodeoxyuridine from immunoliposomes to colon cancer cells. Biochim. Biophys. Acta, 1420: 153-167, 1999; Exploiting Tyrosinase Expression and Activity in Melanocytic Tumors: Quercetin and the Central Role of p53, Integr Cancer Ther Dec. 1, 2011 10:328-340; Molecular Basis of the extreme dilution mottled Mouse Mutation: A Combination Of Coding And Noncoding Genomic Alterations, J Biol Chem Feb. 11, 2005 280:4817-4824; Enzyme-Catalyzed Activation of Anticancer Prodrugs, Pharmacol. Rev. Mar. 1, 2004 56:53-102; Sendovski M, Kanteev M, Ben-Yosef V S, Adir N, Fishman A., First Structures of an Active Bacterial Tyrosinase Reveal Copper Plasticity, Journal of Molecular Biology, Volume 405, Issue 1, 7 Jan. 2011, Pages 227-237; Greta Faccioa, Kristiina Kruusb, Markku Salohеimob, Linda Thöny-Meyera, Bacterial tyrosinases and their applications, Process Biochemistry, Volume 47, Issue 12, December 2012, Pages 1749-1760; Hughes B W, Wells A H, Bebok Z, Gadi V K, Garver R I Jr, Parker W B, Sorscher E J, Bystander killing of melanoma cells using the human tyrosinase promoter to express the Escherichia coli purine nucleoside phosphorylase gene, Cancer Res. 1995 Aug. 1; 55(15):3339-45, each of which is expressly incorporated herein by reference in its entirety.

The present technology provides, according to various embodiments, live attenuated therapeutic bacterial strains that have improved ability compared to a parental strain in regard to the pharmacokinetic properties of enhanced circulation in the bloodstream and entry into, persistence and growth within tumors, by resisting immune elimination or lytic destruction, increased numbers of foci within tumors, increased colonization, expansion and persistence within tumors. It is the intention of these changes that the result in an overall increase in 1) the percentage of tumors targeted, 2) the number of individual locations (foci) within a tumor that are targeted, 3) the number of CFU/g that are found within the tumor, 4) the length of time that they reside within the tumor and 5) reduced immune clearance from the tumor, and, alone or collectively 6) increased antitumor activity.

One object is to select for one or more mutations that result in smaller sized bacteria with improved (increased) pharmacokinetics in blood through reduced elimination and improved penetration though the leaky tumor vasculature.

The present technology also has the objective of utilizing the enhanced permeability and retention (EPR) factor associated with tumor vasculature. To utilize the EPR effect, the bacteria should preferably be smaller than 650 nm in size, and more preferably less than 400 nm in size (Danhier et al., 2010, To exploit the tumor microenvironment: passive and active tumor targeting of nanocarriers for anticancer drug delivery. J. Control. Release 148: 135-146, expressly incorporated herein by reference in its entirety). Preferred bacteria therefore have as their width less than 650 nm, and more preferably less than 400 nm.

Another object is to generate bacteria with a protective sialic acid coat that results in improved (increased) pharmacokinetic half-life in blood, improved penetration though leaky tumor vasculature and reduced immune clearance. The non-limiting mechanisms by which sialic acid prevents immune clearance include reduced opsonization (i.e., reduced interaction with complement, ficolin, manose binding protein, C-reactive protein, scavenger receptor, and/or antibodies) by increasing repulsive interaction with blood components and increasing surface hydrophobicty. The present invention is unlike vaccine vectors that express glycosylated antigens (Szymanski and Nothaft EP2611823, Peptide containing multiple n-linked glycosylation sequons, expressly incorporated herein by reference in its entirety) because the invention is directed toward reduced immune stimulation, detection or elimination, whereas vaccine vectors are designed to be detected and to stimulate the immune system.

Another object is to construct bacteria that alternately express external antigens such as O and H antigens under exogenous control of inducible promoters such that different antigens are controllably expressed at different times and result in bacteria with improved (increased) pharmacokinetics in blood and reduced immune clearance and reduce immune recognition upon repeated dosing.

Another object is to develop bacteria that deliver ligands against programmed cell death protein 1 (PD1) and/or its ligand (PD-L1 and PD-L2) or CTLA-4 which has the result of increased T-cells attacking tumors and increasing the habitable region of the tumor by bacteria through their killing of tumor cells and providing nutrients for the bacteria. Compositions and methods for inhibition of PD-1 or PD-L1/PD-L2 have been described by U.S. Pat. No. 6,803, 192, US 20130202623 and PCT publication No. WO 10/027423 each of which is expressly incorporated by reference in its entirety Another object is to genetically modify the bacteria to express the *E. coli* tryptophanase which results in greater tumor cell killing and enhanced penetration of the bacteria within the tumor.

Another object is to genetically modify the bacteria to express and secrete mammalian or bacterial tyrosinase, as directly toxic principle or as a prodrug-converting enzyme. More broadly, other known prodrug converting enzymes secretable from the bacteria (e.g., *Salmonella*) may be employed, such as cytosine deaminase. Similarly, essential biochemical depleting enzymes may also be expressed, such as asparginase.

Another object is to increase serum resistance to components that act as opsonins which enhance elimination by phagocytic cells or directly interfere with or kill bacteria, including complement, antibodies, ficolin, scavenger receptor, C-reactive protein (CRP), the bactericidal/permeability-increasing protein (BPI) and mannose binding protein, by reducing their binding or prevention of their mode of action including resisting lytic destruction. The bacteria are selected for as previously described by Pawelek et al., WO/1996/040238, expressly incorporated herein by reference in its entirety, where the bacteria are recycled through tumors. The bacteria are further cycled one or more times through the blood (for selection of increased serum half-life and survival by selecting for their presence at extended times) and through the liver (for selection of increased survival against serum components and/or carbon dioxide ($CO_2$), bicarbonate ($HCO^{3-}$), carbonate ($CO_3^{2-}$) and/or carbonic acid ($H_2CO_3$ or $OC(OH)^2$). The vertebrates useful for cycling include mice, rats, guinea pigs, rabbits, dogs, cats, pigs, monkeys and humans. The subjects may be further exposed to carbogen (carbon dioxide and oxygen mixtures) during the selection. The selection may also take place ex vivo (i.e., blood drawn from a patient, or blood fed into a chemostat).

A further object provides a genetically engineered bacterium, optionally being genetically selected or mutated to have a reduced size compared to its parental strain, comprising at least one gene which causes or induces carbohydrate decoration of external components of the genetically engineered bacterium, being adapted for efficacious treatment of a neoplastic disease in the human or animal under non-lethal conditions.

The at least one gene may comprises at least one heterologous gene that produces sialic acids on an external surface of the bacterium.

The genetically engineered bacterium may further comprise inducible gene promoters adapted to control the genetically engineered bacterium to display heterologous surface antigens. The inducible surface antigens may be O-oligosaccharide antigens and/or flagellar (H) antigens.

The genetically engineered bacterium may comprise genetic modifications for producing a plurality of heterologous surface antigens on the genetically engineered bacterium, which are produced by the genetically engineered bacterium under control of multiple different inducible promoters.

The genetically engineered bacterium may comprise genetic modifications for producing a plurality of different heterologous surface antigens on a surface of the genetically engineered bacterium, which are all under control of an acetylsalicylic acid inducible promoter.

The parental strain comprises a bacterium of genus *Salmonella*, e.g., VNP 20009/YS1646.

The genetically engineered bacterium may be selected or mutated to grow to a maximum size of about 650 nm.

The neoplastic disease comprises may be disease associated with formation of a solid tumor in a host animal, e.g., having necrotic regions.

Administration of the genetically engineered bacterium to the human or animal may result in at least one of: increased numbers of colony forming units within the solid tumor compared to its parental strain; increased serum half-life compared to its parental strain; increased numbers of colony forming units within the solid tumor compared to its parental strain; and reduced immune elimination following repeated dosing compared to its parental strain.

The live genetically engineered bacterium may be provided in a pharmaceutically acceptable formulation suitable for administration to a human or animal, and the carbohydrate decoration of external components of the genetically engineered bacterium is effective for increasing a serum half-life of the live genetically engineered bacterium after administration to the human or animal in the pharmaceutically acceptable formulation.

It is also an object to provide a bacterium genetically engineered to provide an acetylsalicylic acid inducible promoter, which promotes expression of at least one antitumor protein by the bacterium. The bacterium may also have at least one gene which is heterologous, selected or mutated, optionally responsive to an acetyl salicylic acid inducible promoter or the same promoter as the at least one antitumor protein, which causes the bacterium to be decorated with carbohydrates in a heterologous decoration pattern. The at least one gene may comprise a plurality of genes, each responsive to an acetyl salicylic acid inducible promoter, effective for causing the bacterium to selectively display a different heterologous antigen in response to presence of acetyl salicylic acid.

The bacterium may comprise at least one gene which is heterologous, selected or mutated, which causes the bacterium to be decorated with carbohydrates in a heterologous decoration pattern.

A still further object provides a method for treating a neoplastic disease in a living human or animal, comprising: administering a pharmaceutically acceptable formulation containing a genetically engineered bacterium to the living human or animal having the neoplastic disease, the genetically engineered bacterium may optionally be genetically engineered or selected to have a reduced size compared to its parental strain and which grows to a maximum size of about 650 nm, having at least one gene which causes or induces carbohydrate decoration of external components of the genetically engineered bacterium in a pattern different from the parental strain; permitting the genetically engineered bacterium to grow within and then be cleared from the living human or animal to cause antitumor effects, which are non-lethal to the living human or animal.

Administration of the pharmaceutically acceptable formulation containing a genetically engineered bacterium to the human or animal may result in at least one of: increased numbers of colony forming units within the solid tumor compared to its parental strain; increased serum half-life compared to its parental strain; increased numbers of colony forming units within the solid tumor compared to its parental strain; and reduced immune elimination following repeated dosing compared to its parental strain.

The at least one gene may comprise at least one heterologous gene that produces sialic acids on an external surface of the bacterium.

The genetically engineered bacterium may further comprise inducible gene promoters adapted to control the genetically engineered bacterium to display at least one of heterologous O-oligosaccharide surface antigens and flagellar (H) antigens, further comprising inducing the inducible gene promoters.

Another object provides a live genetically engineered bacterium, comprising: at least one heterologous inducible gene which causes or induces carbohydrate decoration of external components of the live genetically engineered bacterium, at least one gene producing a functional gene product under control of an inducible promoter distinct from the at least one heterologous inducible gene, the live genetically engineered bacterium being adapted for administration to a human or animal and colonization of at least one tissue under non-lethal conditions.

The carbohydrate decoration may comprise sialic acid, O-oligosaccharide antigens, and/or H flagellar antigens, for example.

The gene product may comprise an enzyme which is secreted from the live genetically engineered bacterium in active form, such as an amino-acid degrading enzyme (e.g., tryptophanase, asparaginase) which is secreted from the live genetically engineered bacterium in active form and has anti-tumor activity against human or animal tumors colonized by the live genetically engineered bacterium.

The inducible promoter may comprise MarA, which is induced by presence of acetyl salicylic acid. The inducible promoter may also be responsive to at least one of tet, arabinose, hypoxia, a cellular SOS response promoter, X-rays, and mitomycin.

The at least one heterologous inducible gene which causes or induces carbohydrate decoration of external components of the genetically engineered bacterium may comprise a plurality of inducible genes having respectively different inducers. At least one of the plurality of inducible genes having respectively different inducers may be responsive to a pharmacological inducer which is not naturally found in human tissue. The at least one heterologous inducible gene and the at least one gene producing a gene product under control of an inducible promoter may each induced by a common inducer. The at least one heterologous inducible gene may comprise a plurality of inducible genes, having respectively different inducible promoters induced by different pharmacological agents not naturally found in humans, to thereby provide the live genetically engineered bacterium having a plurality of different surface antigen patterns under control of a selective presence of the different pharmacological agents.

The live genetically engineered bacterium may have a selective tropism for at least one type of tumor in a human or animal, and the functional gene product is effective for treating the at least one type of tumor, the live genetically engineered bacterium being provided within a pharmaceutically acceptable formulation for administration to the human or animal.

The genetically engineered bacterium may further comprise a heterologous acetyl salicylic acid inducible gene promoter adapted to control the genetically engineered bacterium to produce a gene product, further comprising administering acetylsalicylic acid to the human or animal to induce the gene product.

When administering self-replicating organisms, the minimum dose approximates a single in vivo replication competent organism or minimum infectious dose, which itself is approximated by an in vitro determined colony forming unit (CFU). Suitable dosage ranges are generally from about 1.0 c.f.u./kg to about $1\times10^{10}$ c.f.u./kg; optionally from about 1.0 c.f.u./kg to about $1\times10^{8}$ c.f.u./kg; optionally from about $1\times10^{2}$ c.f.u./kg to about $1\times10^{8}$ c.f.u./kg; optionally from about $1\times10^{4}$ c.f.u./kg to about $1\times10^{8}$ c.f.u./kg; and optionally from about $1\times10^{4}$ c.f.u./kg to about $1\times10^{10}$ c.f.u./kg. Effective doses may be extrapolated from dose-response curves derived from in vitro or animal model test systems. However, higher doses are preferred, in order to permit prompt initiation of therapeutic effect and avoid host immune response suppression of the organisms before they reach full therapeutic potential. In some cases, replication incompetent organisms may be used, e.g., where the organisms remain competent to produce biologically active products as discussed herein while not being able to replicate, in which case a dose may be, for example, in the range $10^{8}$ to $10^{10}$ organisms and determined by non-culture based methods (e.g., hemocytometer). The maximum dose of preferred organisms which display low toxicity and pathogenicity is in excess of $10^{10}$, and for orally or dermally administered probiotic species, gram scale doses may be administered.

The bacterial delivery vector may be attenuated, non-pathogenic, low pathogenic (including wild type), or a probiotic bacterium. The bacteria are introduced either systemically (e.g., parenteral, intravenous (IV), intramuscular (IM), intralymphatic (IL), intradermal (ID), subcutaneously (sub-q), local-regionally (e.g., intralesionally, intratumorally (IT), intraperitoneally (IP), topically, intathecally (intrathecal), by inhaler or nasal spray) or to the mucosal system through oral, nasal, pulmonary intravessically, enema or suppository administration. The terms "oral", "enteral", "enterally", "orally", "non-parenteral", "non-parenterally", and the like, refer to administration of a compound or composition to an individual by a route or mode along the alimentary canal. Examples of "oral" routes of administration include, without limitation, swallowing liquid or solid forms by the mouth, administration of a composition through a nasojejunal or gastrostomy tube, intraduodenal administration of a composition, and rectal administration, e.g., using suppositories that release a live bacterial strain described herein to the lower intestinal tract of the alimentary canal. Upon administration, the bacteria are able to undergo limited or unlimited replication, express, surface display, secrete and/or release the effector molecules and/or protease inhibitors with anti-cancer thereby providing a therapeutic benefit by reducing or eliminating the malignancy and/or neoplasia.

Bacteria of the invention have recognizable attributes in regard to their serum half-life and presence within tumors. For example, Toso et al., 2002 (Phase I Study of the Intravenous Administration of Attenuated *Salmonella typhimurium* to Patients with Metastatic Melanoma, Journal of Clinical Oncology, 20: 142-152, expressly incorporated herein by reference in its entirety) showed for example that a dose of $3\times10^{8}$ of the strain VNP20009 resulted in an average (in 6 patients) of approx. 65,000 CFU per ml of blood at 25 min, but only an average of 19 CFU/ml at 60 min., and only an average of 0.1 CFU/ml at 4 hrs, and only one patient in 6 had any CFU/ml at 12 hrs. Bacteria of the invention have significantly higher numbers of colony forming units at one or more times following 25 min, or have higher numbers of patients with greater than 0 CFU/ml at 12 hrs. A single patient in that treatment group received a second dose: that patient had 19,400 CFU/ml at 25 min for the first dose, but only 38 CFU/ml for the second dose.

Bacteria of the invention have significantly greater numbers of CFU/ml at 25 min upon subsequent doses. Patients in that same treatment group were also assessed for the presence of CFU/g of tumor tissue. Only one in six patients had any CFU/g in their tumor. Bacteria of the invention have significantly greater percentages of tumors colonized by bacteria. The one tumor that was colonized by the bacteria had 11,000 CFU/g of tumor tissue, compared to $10^9$ CFU/g in tumor tissue of mice (Luo et al., 2001, Antitumor effect of VNP20009, an attenuated *Salmonella* in murine tumor models. Oncol. Res. 12: 501-508, expressly incorporated herein by reference in its entirety). Bacteria of the invention have significantly CFU/g of tumor tissue. In the study by Toso et al., 2002, no antitumor activity was observed, whereas the bacteria of the invention have improved antitumor activity.

4. BRIEF DESCRIPTION OF THE DRAWINGS

5. DETAILED DESCRIPTION OF THE INVENTION

Figure 1A:
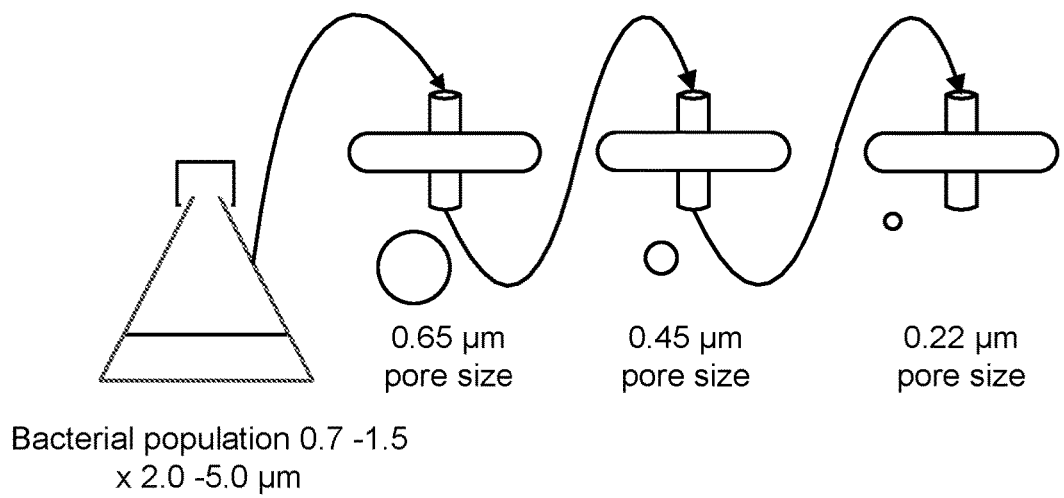
FIGS. 1A-1C show schematically a method for selection of bacteria with reduced size.
Figure 1B:
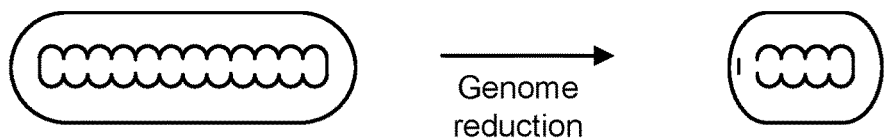
Figure 1C:
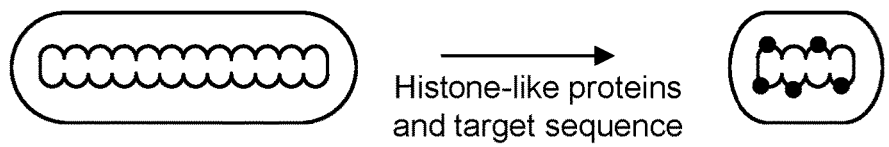

The present invention provides, according to various embodiments, bacteria with enhanced pharmacokinetics that have improved ability to distribute systemically, to persist longer within tumors, target tumors in multiple foci, targeted higher percentages of tumors, target tumors with increased numbers of bacteria, remove tumor cell immunosuppressive functions, increase the antitumor immune response and have enhanced tumor cell killing that alone or in combination, and result in increased antitumor activity.

For reasons of clarity, the detailed description is divided into the following subsections: 1) bacteria with reduced size, 2) bacteria with a protective sialic acid coat, 3) bacteria that alternately express external antigens such as O and H antigens under exogenous control of inducible promoters, 4) bacteria that deliver anti-immunosuppressive ligands against CTLA-4, programmed cell death protein 1 (PD1) and programmed cell death ligand (PD-L1) and 5) bacteria that express tryptophanase.

The present technology provides, according to various embodiments, improved live attenuated therapeutic bacterial strains that express one or more therapeutic molecules. The primary characteristic of the bacteria of certain embodiments of the invention is the improved targeting to tumors and reduced clearance from the blood (increased serum half-life) with enhanced antitumor activity. In one embodiment, the percent increase in effect is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% greater than the parental strain of bacteria without expressing one or more of the modifications described herein under the same conditions.

5.1. Bacteria with Reduced Size.

Typical *Salmonella* are gram-negative rods 0.7-1.5 by 2.0-5.0 μm. *Salmonella* of the invention having smaller size are derived by several different means. Bacteria with smaller size are selected for their ability to pass thorough microporous sterilizing membranes followed by light and electron microscopic analysis. Because of their size, *Salmonella* do not typically pass through 0.65, 0.45 or 0.22 uM porous filters. The bacteria are thus selected for their ability to pass through successively smaller pore sizes. The present technology and methods may be used alone or in combination and with or without the FabH mutation known to reduce bacterial size (Wootton, 2012, Nature Rev. Microbiol. 10: 670-671, expressly incorporated herein by reference in its entirety). The bacteria may be further cycled through tumors as described by Pawelek et al. (U.S. Pat. No. 6,190,657 Vectors for the Diagnosis and Treatment of Solid Tumors Including Melanoma), expressly incorporated herein by reference in its entirety.

5.1.1. Bacterial Mutations.

Bacteria may be isolated by random mutagenesis using UV and nitrosoguanidine, or by transposon mutagenisis and selected for smaller size as described above. Alternatively, unsuppressed msbB strains (YS1; Murray et al., 2001, Extragenic suppressors of msbB⁻ growth defects in *Salmonella*. J. Bacteriol. 183: 5554-5561) or partially suppressed msbB strains (Murray et al., 2007. PmrA(Con) Confers pmrHFIJKL-Dependent EGTA and Polymyxin Resistance on msbB *Salmonella* by Decorating Lipid A with Phosphoethanolamine. J. Bacteriology, 189: 5161-5169; Murray et. al., 2004 Hot spot for a large deletion in the 18-19 Cs region confers a multiple phenotype in *Salmonella enterica* serovar *Typhimurium* strain ATCC 14028, J. Bacteriol, 186: 8516-8523, each of which is expressly incorporated herein by reference in its entirety) may be used to selected for spontaneous mutations or combination of selections thereof. The mutations can be identified by methods known to those skilled in the arts including genome sequencing.

5.1.2. Bacteria with Reduced Genome Size.

Bacteria with reduced genomes are generated by selecting for loss of functions that are associated with phenotypic markers. Methods are known to those skilled in the arts (Posfai et al., 2006, Emergent properties of reduced-genome *Escherichia coli*, Science 312: 1044-1046; Campbell et al., U.S. Pat. No. 8,178,339, Reduced genome *E. coli*, each of which is expressly incorporated herein by reference in its entirety) and selected for smaller size as described above.

5.1.3. Bacteria with Tighter Genome Packaging.

Bacteria with tighter genome packaging are produced by, e.g., 1) introducing the *Chlamydia* specific histone-like protein binding sequences

SEQ ID NO: 001
AATAGGGTTTCTTTTAATAGAAAC and

SEQ ID NO: 002
AATAGGGATTCCAGTAACAACAAG into the chromosome using methods known to those skilled in the art (e.g., transposons, sucrose vector insertions, lambda red vector insertions) and heterologously expressing the *Chlamydia* (e.g., Genbank: CP002679.1) histone H1-I, histone-like proteins HC1 and HC2 or homologs or variants thereof (e.g., GenBank: L10193.1 Hc2 nucleoproteins hctB) using methods known to those skilled in the arts, and selecting for smaller size as described above.

5.2. Bacteria with a Protective Sialic Acid Coat.

The bacteria are engineered to be coated with sialic acid either by A) de novo synthesis or B) scavenged from the host. De novo synthesis of lipopollysaccharide with sialic acid is accomplished by heterologous expression of the genes necessary including but not limited to NeuA, NeuB, NeuC, SiaB, Lic3A, Lic3B, and SOAT (sialic acid O-acyltransferase) as described by Severi et al., 2007 (Sialic acid utilization by bacterial pathogens, Microbiology 153: 2817-2822). De novo synthesis of a polysaccharide capsule with sialic acid is accomplished by the additional heterologous expression of NeuD, NeuS, NeuO, and Kps (capsule export system). Scavenging of sialic acid requires the additional presence of a sialidase, NanC, porins, SatABCD, SiaPQM and NanT. Heterologous expression is achieved using synthetic biology and methods known to those skilled in the art.

5.3. Bacteria that Alternately Express Surface Antigens Such as O and H Antigens Under Exogenous Control of Inducible Promoters.

The diverse range of *Salmonella* serotypes contains a variety of O-polysaccharide (O-antigen) and flagellar (H antigens) (Grimont, P. A. D & Weill, F. X. 2007. Antigenic Formulae of the *Salmonella* Serovars, WHO Collaborating Centre for Reference and Research on *Salmonella*, 9th edition). Exposure of the host to these antigens may lead to protective immunity. In the context of bacterial vectors, protective immunity may either eliminate the vector thereby reducing its antitumor effect or prevent secondary and tertiary dosing. The present technology provides a single bacterium that inducibly undergoes alternate expression of O and H antigens, alone or in simultaneous combination. Methods for deriving heterologous 0-antigens have been described by Favre et al., WO/1997/014782, and Roland WO/2000/004919, each of which is expressly incorporated herein by reference in its entirety. O-antigen synthesis is directed by the rfb gene cluster which encodes enzymes involved in biosynthesis of the monomer sugar unit, and the rfc gene, which encodes the O-antigen polymerase responsible for the polymerization of the sugar unit into a high molecular weight polysaccharide chain (Sugiyama et al., 1991 Expression of the Cloned *Escherichia coli* 09 rfb Gene in Various Mutant Strains of *Salmonella typhimurium*, J. Bacteriol. 173:55-58; Collins et al. 1991, Molecular Cloning, Characterization, and Nucleotide Sequence of the rfc Gene, Which Encodes an O-Antigen Polymerase of *Salmonella typhimurium*, J. Bacteriol. 173:2521-2529, each of which is expressly incorporated herein by reference in its entirety). The antigens are chosen such that alternate expression does not have overlap. For example the O-antigens of the *S. typhimurium* serovar are O: 1, 4, 5, 12, whereas those of *S. Montevideo*, O: 6, 7, and those of $E_3$ group are O: 3, 15, 34. The genes may be part of a single synthetic operon (polycistronic), or may be separate, monocystronic constructs, with separate individual promoters of the same type used to drive the expression of their respective genes. The promoters may also be of different types, with different genes expressed by different constitutive or f promoters. Use of two separate inducible promoter for more than one antigen allows, when sufficient X-ray, tetracycline, arabinose methylalicylate or other inducer is administered following administration of the bacterial vector, their expression to occur simultaneously, sequentially, or alternating (repeated). A variety of inducible promoters are known including arabinose, (EP1,655,370 A1, expressly incorporated by reference in its entirety), tetracycline inducible promoter (TET promoter), SOS-response promoters responsive to DNA damaging agents such as mitomycin, alkylating agents, X-rays and ultraviolet (UV) light such as the recA promoter, colicin promoters, sulA promoters and hypoxic-inducible promoters including but not limited to the PepT promoter (Bermudes et al., WO 01/25397, expressly incorporated herein by reference in its entirety), the arabinose inducible promoter ($Ara_{BAD}$) (Lossner et al., 2007, Cell Microbiol. 9: 1529-1537; WO/2006/048344) the methylsalicylate inducible promoter (Royo et al., 2007, Nature Methods 4: 937-942; WO/2005/054477, each of which is expressly incorporated herein by reference in its entirety). A single promoter may be used to drive the expression of more than one antigen gene, such multiple O-antigens O: 1, 4, 5, 12 engineered to be present on the chromosome. To achieve multiple alternating sets of antigens, coexistence of a set of alternative, non-overlapping antigens such as O: 6, 7 under control of a separate inducible promoter are constructed. Thus, a bacterial culture may be induced to have one set of antigens for a first injection, and may be induced to have a second set of antigens for a second injection, and so on. Similarly, following a first injection with induced expression of one set of antigens, the first inducer may be curtailed, and the inducer for the second set of antigens initiated, thus avoiding prolonged exposure to the immune systems and avoiding immune elimination.

A novel acetylsalicylic acid (aspirin)-inducible promoter is also encompassed based upon the *Salmonella* multiple antibiotic resistance operon (mar) promoter/operator regulon (Sulavik et al., 1997, The *Salmonella typhimurium* mar locus: molecular and genetic analyses and assessment of its role in virulence. J. Bacteriol. 179: 1857-1866; Barbosa and Levy, 2000 Differential expression of over 60 chromosomal genes in *Escherichia coli* by constitutive expression or MarA, J. Bacteriol 182: 3467-3474; Alekshun and Levy, 2004, The *Escherichia coli* mar locus-antibiotic resistance and more, ASM News 70: 451-456), Genbank accession number U54468.1 (which, by itself, does not confer antibiotic resistance), each of which is expressly incorporated herein by reference in its entirety. The regulon consists of the mar promoter/operator region, the MarR negative regulator, the MarA positive regulator, and the downstream start codon (ATG) that is used for expression of the gene(s) of interest such as the rfb cluster. Alternatively, use of the mar regulon also encompasses inducible expression of other anti-cancer proteins, protease inhibitors and targeted toxins and antitumor enzymes and/or genetically engineered phage and phagemids (Bermudes U.S. Pat. No. 8,524,220, Protease Inhibitor: Protease sensitivity expression system composition and methods improving the therapeutic activity and specificity of proteins delivered by bacteria; U.S. Pat. No. 8,241,623, Protease Sensitivity Expression System; U.S. Pat. No. 8,623,350 Protease inhibitor: protease sensitivity expression system and method improving the therapeutic activity and specificity of proteins and phage and phagemids delivered by bacteria) or combinations with antivascular agents, such as platelet factor 4 and thrombospondin, alone or in combination (Bermudes et al., U.S. Pat. No. 6,962,696, U.S. Pat. No. 7,452,531 Compositions and Methods for Tumor-Targeted Delivery of Effector Molecules) and other anticancer agents (e.g., WO2009/126189, WO03/014380, WO/2005/018332, WO/2008/073148, US 2003/0059400 U.S. Pat. Nos. 7,452,531, 7,354,592, 6,962,696, 6,923,972, 6,863,894, 6,685,935, 6,475,482, 6,447,784, 6,190,657 and 6,080,849, each of which is expressly incorporated herein by reference in its entirety). The DNA containing the upstream regulon promoter/operator, the MarR and MarA genes and ending with the start codon (ATG; caps) to which may be fused as the initiating codon a gene or genes of interest is encompassed by:

SEQ ID NO: 003
```
cagtgtgcaagttaatatcctctacaacctataacctgtaattatcaatt
agttacaagttatcacagcacaatacccggacgccttttagcaaatcgt
ggcatcggccaattcatttagttgacttatacttgcctgggcaatagtat
ctgacgaaattaattacttgccggggcaaccattttgaaaagcaccagtg
atctgttcaATGaaatcattccgctgggtcgcttgatctacatggtaaat
cagaaaaagatcgcctgttaaataactatttatccccgctggatatcac
cgcaacacagtttaaagtgctttgctcgatacgctgcgcgggatgtatta
ccccggttgaacttaaaaaagtgctgtctgtcgatctcggcgcattgacg
cggatgctcgaccgcctgctgtgcaaaggctggatcgaaagactgccgaa
tcctaatgacaaacgcggcgtactggtgaagctaacgccggacggcgcgg
caatttgtgagcaatgtcatcaacgaccagggcaagacctgcatcaggaa
ttaacaaaaacttaacggcggacgaagtggcaacgcttgagtatttgct
caagaaaattctgccgtagacaaaaaagaggtATGacgatgtccagacgc
aacactgacgctattactattcatagcattttggactggatcgaggataa
cctggagtcgccgctctcactggaaaaagtgtctgagcgttcaggatatt
ccaaatggcacctgcaacggatgtttaaaaaagagaccggtcattcatta
ggccaatacatccgcagccgtaaaatgacggaaatcgcgcaaaaattaaa
agagagcaacgagcccattctctatctggcggaacgctatggctttgagt
cacagcaaacattgacccggacgttcaaaaactattttgatgtgccgcca
cacaaataccggatcaccaatatgcatggcgaatcacggtatatgctgcc
gctgaaccatggcaactactagtttgtttatgcgccacgcgaagagcacc
ATG
```

In another embodiment, the Seq. ID NO.:003 bp 1-209, with the ATG of MarR at 210-212 is used as the start codon. In a more preferred embodiment, the Seq. ID NO.:003 bp 1-632, with the ATG of MarA at 633-635 is used as the start codon. Optionally, in any of the promoters described above, a bacterial termination sequence can be placed upstream of bp 1 (Peters et al., 2011 Bacterial transcriptional terminators: the RNA3' end chronicals, J. Mol. Biol. 412: 793-813), expressly incorporated herein by reference in its entirety.

5.4. Bacteria that Deliver Ligands Against Immunosuppressive Factors Including Programmed Cell Death Protein 1 Ligand (PD-L1), PD-L1 Receptor (PD-1) or CTLA-4.

Bacteria that reside within tumors rely upon nutrients obtained from the host. While necrotic tissue formed due to tissue hypoxia is believed to be one of the primary sources of nutrients for bacteria colonizing tumors, cell death due to immune functions such as those of cytotoxic T-cells attaching tumor cells also have the potential to contribute to the growth and expansion of intratumoral bacteria by providing nutrients. An object of one embodiment of the technology is to use the bacteria described herein alone or in combination with other aspects of the technology that increase the bacteria's ability to colonize and expand within tumors. Ligands against immuno-suppressive factors such PD-L1 and CTLA-4 include antibodies, affibodies (protein A affinity-based ligands), armadillo repeat protein-based scaffolds, adnectins, anticalins, lipocalins, Kunitz domain-based binders, avimers, knottins, fynomers, atrimers and DARPins (designed ankyrin repeat proteins) and cytotoxic T-lymphocyte associated protein-4 (CTLA4)-based binders (Weidle et al., 2013 The emerging role of new protein scaffold-based agents for treatment of cancer. Cancer Genomics Protomics 10: 155-168, expressly incorporated herein by reference in its entirety). Ligands such as those against PD-L1 such as those described by Gao et al., 2014 (Small peptides elicit anti-tumor effects in CT26 model through blocking PD-L1/PD-1 (TUM2P.900, Journal of Immunology 192 (1 Supplement) 71.24) are expressed using secretion proteins described above, such as fusions with YebF. Anti-CLA-4 anticalin PRS-010 is also engineered as a YebF fusion, and may optionally contain a protease cleavage site for release of the anticalin within the tumor. CLA-4 anticalins may also be expressed by filamentous phage or as bacterial surfface displayed (WO2012072806A1; Muteins of human liopcalin 2 with affinity for CTLA-4; 20090042785 Compound with affinity for the cytotoxic T lymphocyte-associated antigen (CTLA-4; 20100285564 Anticalins; 20100160612 Muteins Of Tear Lipocalin With Affinity For The T-Cell Coreceptor CD4, each of which is expressly incorporated herein by reference in its entirety). Affibodies are generated as described by Felwisch and Tomachev 2012, Enginnering of affibody molecules for therapy and diagnosis. Methods Molecular Biol 899: 103-126). DARPins are designed and screened for as previously described (Stumpp and Amstutz 2007, DARPins: a true alternative to antibodies, Curr Opin Drug Discov. Devel. 10: 159-153; Zahnd et al., 2010, Efficient tumor targeting with high-affinity designed ankyrin repeat proteins: Effects of Affinity and Molecular Size, Cancer Res 2010; 70:1595-1605; WO/2013022091 Therapeutic Agent For Autoimmune Diseases Comprising PD-1 Agonist), each of which is expressly incorporated herein by reference in its entirety. The localized production of the PD-L1 or CTLA-4 agonists is distinctly different than systemic administration of agonists such as antibodies, because systemic administration of PD-L1 or CTLA-4 agonists has the potential to have systemic immune collateral damages, whereas the intratumoral production limits the T-cell response to the tumor environment. Combination with smaller size bacteria, alternating surface antigens and tryptophanase (see below) further enhance the overall antitumor effect.

5.5. Bacteria that Express the Tryptophanase.

Bacterial production of metabolites that are toxic to tumor cells such as indol, a product of tryptophanase, is used to enhance bacterial spread within the tumor by killing tumor cells by the production of the indol metabolite that the bacteria are not themselves affected by. The tumor cells are further starved for tryptophane by the depletion of tryptophan by tryptophanase. The combination of these effects is further enhanced by the other pharmacokinetic enhancements, tumor penetration, persistence and intra-tumoral spreading. Expression of tryptophanase may use the *Escherichia coli* genes or any homologous genes; those of the enterobacteriaceae are a preferred embodiment. In *E. coli* which are encoded by a transcribed leader region, tnaL (also known as tnaC), and two larger structural genes, where tnaA, which encodes the degradative enzyme and tnaB which together with the tnaL product are involved in tryptophane transport. In *E. coli* the genes exist as an operon and are expressed using a single promoter, such as the constitutive promoter or an inducible promoter. Alternatively, the endogenous tryptophanase or a modified tryptophanase promoter (Sitney et al., 1996, Use of a Modified Tryptophanase Promoter to Direct High-Level Expression of Foreign Proteins in *E. coli*, Ann. N.Y. Acad. Sci. 782: 297-310, expressly incorporated herein by reference in its entirety) may be used. The genes encode the 3 peptides:

TnaL (TnaC): MNILHICVTSKWFNIDNKIVDHRP
SEQ ID NO: 004

TnaA:
SEQ ID NO: 005
MENFKHLPEPFRIRVIEPVKRTTRAYREEAIIKSGMNPFLLDSEDVFIDL
LTDSGTGAVTQSMQAAMMRGDEAYSGSRSYYALAESVKNIFGYQYTIPTH
QGRGAEQIYIPVLIKKREQEKGLDRSKMVAFSNYFFDTTQGHSQINGCTV
RNVYIKEAFDTGVRYDFKGNFDLEGLERGIEEVGPNNVPYIVATITSNSA
GGQPVSLANLKAMYSIAKKYDIPVVMDSARFAENAYFIKQREAEYKDWTI
EQITRETYKYADMLAMSAKKDAMVPMGGLLCMKDDSFFDVYTECRTLCVV
QEGFPTYGGLEGGAMERLAVGLYDGMNLDWLAYRIAQVQYLVDGLEEIGV
VCQQAGGHAAFVDAGKLLPHIPADQFPAQALACELYKVAGIRAVEIGSFL
LGRDPKTGKQLPCPAELLRLTIPRATYTQTHMDFIIEAFKHVKENAANIK
GLTFTYEPKVLRHFTAKLKEV

TnaB:
SEQ ID NO: 006
MTDQAEKKHSAFWGVMVIAGTVIGGGMFALPVDLAGAWFFWGAFILIIAWF
SMLHSGLLLLEANLNYPVGSSFNTITKDLIGNTWNIISGITVAFVLYILTY
AYISANGAIISETISMNLGYHANPRIVGICTAIFVASVLWLSSLAASRITS
LFLGLKIISFVIVFGSFFFQVDYSILRDATSSTAGTSYFPYIFMALPVCLA
SFGFHGNIPSLIICYGKRKDKLIKSVVFGSLLALVIYLFWLYCTMGNIPRE
SFKAIISSGGNVDSLVKSFLGTKQHGIIEFCLLVFSNLAVASSFFGVTLGL
FDYLADLFKIDNSHGGRFKTVLLTFLPPALLYLIFPNGFIYGIGGAGLCAT
IWAVIIPAVLAIKARKKFPNQMFTVWGGNLIPAIVILFGITVILCWFGNVF
NVLPKFG

The complete sequence of the coding region from the start of the first peptide to the stop of the 3<sup>rd</sup> peptide is:

SEQ ID NO: 007
ATGaatatcttacatatatgtgtgacctcaaaatggttcaatattgacaa
caaaattgtcgatcaccgcccttgatttgccttctgtagccatcaccag
agccaaaccgattagattcaatgtgatctatttgtttgctatatcttaat
tttgccttttgcaaaggtcatctctcgtttatttacttgttttagtaaat
gatggtgcttgcatatatctggcgaattaatcggtatagcagatgtaa
tattcacagggatcactgtaattaaaataaatgaaggattatgtaatgga
aaactttaaacatctccctgaaccgttccgcattcgtgttattgagccag
taaaacgtaccactcgcgcttatcgtgaagaggcaattattaaatccgt
atgaacccgttcctgctggatagcgaagatgtttttatcgatttactgac
cgacagcggcaccggggcggtgacgcagagcatgcaggctgcgatgatgc
gcggcgacgaagcctacagcggcagtcgtagctactatgcgttagccgag tcagtgaaaaatatctttggttatcaatacaccattccgactcaccaggg
ccgtggcgcagagcaaatctatattccggtactgattaaaaaacgcgagc
aggaaaaaggcctggatcgcagcaaaatggtggcgttctctaactatttc
tttgataccacgcagggccatagccagatcaacggctgtaccgtgcgtaa
cgtctatatcaaagaagccttcgatacgggcgtgcgttacgactttaaag
gcaactttgaccttgagggattagaacgcggtattgaagaagttggtccg
aataacgtgccgtatatcgttgcaaccatcaccagtaactctgcaggtgg
tcagccggtttcactggcaaacttaaaagcgatgtacagcatcgcgaaga
aatacgatattccggtggtaatggactccgcgcgctttgctgaaaacgcc
tatttcatcaagcagcgtgaagcagaatacaaagactggaccatcgagca
gatcacccgcgaaacctacaaatatgccgatatgctggcgatgtccgcca
agaaagatgcgatggtgccgatgggcggcctgctgtgcatgaaagacgac
agcttctttgatgtgtacaccgagtgcagaaccctttgcgtggtgcagga
aggcttcccgacatatggcggcctggaaggcggcgcgatggagcgtctgg
cggtaggtctgtatgacggcatgaatctcgactggctggcttatcgtatc
gcgcaggtacagtatctggtcgatggtctggaagagattggcgttgtctg
ccagcaggcgggcggtcacgcggcattcgttgatgccggtaaactgttgc
cgcatatcccggcagaccagttcccggcacaggcgctggcctgcgagctg
tataaagtcgccggtatccgtgcggtagaaattggctctttcctgttagg
ccgcgatccgaaaaccggtaaacaactgccatgcccggctgaactgctgc
gtttaaccattccgcgcgcaacatatactcaaacacatatggacttcatt
attgaagcctttaaacatgtgaaagagaacgcggcgaatattaaaggatt
aaccttacgtacgaaccgaaagtattgcgtcacttcaccgcaaaactta
aagaagtttaattaatactacagagtggctataaggatgttagccactct
cttaccctacatcctcaataacaaaaatagccttcctctaaaggtggcat
catgactgatcaagctgaaaaaaagcactctgcattttggggtgttatgg
ttatagcaggtacagtaattggtggaggtatgtttgctttacctgttgat
cttgccggtgcctggttttttctggggtgcctttatccttatcattgcctg
gttttcaatgcttcattccgggttattgttattagaagcaaatttaaatt
atcccgtcggctccagttttaacaccatcaccaaagatttaatcggtaac
acctggaacattatcagcggtattaccgttgccttcgttctctatatcct
cacttatgcctatatctctgctaatggtgcgatcattagtgaaacgatat
caatgaatttgggttatcacgctaatccacgtattgtcgggatctgcaca
gccatttcgttgccagcgtattgtggttaagttcgttagccgccagtcg
tattacctcattgttcctcgggctgaagattatctcctttgtgatcgtgt
ttggttcttttttcttccaggtcgattactccattctgcgcgacgccacc
agctccactgcgggaacgtcttacttcccgtatatctttatggctttgcc
ggtgtgtctggcgtcatttggtttccacggcaatattcccagcctgatta
tttgctatggaaaacgcaaagataagttaatcaaaagcgtggtatttggt
tcgctgctggcgctggtgatttatctcttctggctctattgcaccatggg -continued
```
gaatattccgcgagaaagctttaaggcgattatctcctcaggcggcaacg ttgattcgctggtgaaatcgttcctcggcaccaaacagcacggcattatc gagttttgcctgctggtgttctctaacttagctgttgccagttcgttctt tggtgtcacgctggggttgttcgattatctggcggacctgtttaagattg ataactcccacggcgggcgtttcaaaaccgtgctgttaaccttcctgcca cctgcgttgttgtatctgatcttcccgaacggctttatttacgggatcgg cggtgccgggctgtgcgccaccatctgggcggtcattattcccgcagtgc ttgcaatcaaagctcgcaagaagtttcccaatcagatgttcacggtctgg ggcggcaatcttattccggcgattgtcattctctttggtataaccgtgat tttgtgctggttcggcaacgtctttaacgtgttacctaaatttggcTAA
```

It is understood that other enzymes, such as tyrosinase, may be genetically engineered within the *Salmonella*, instead of or together with the tryptophanase, in accordance with known principles and the discussion herein.

5.6. Bacteria with Enhanced Resistance to Serum.

Bacterial with enhanced resistance to serum and serum components are derived by several additional means, and can be used alone or in combination with sialic acid modifications and/or $CO_2$ resistance.

5.6.1. Selection for increased serum half-life. Mutants can be selected from spontaneous populations, or mutagenized populations as described above. Bacteria with improved serum half-life can be selected by taking blood samples and selecting the bacteria that are found at the tail end of the serum circulation, re-injecting the same bacteria after regrowth, and again selecting for bacteria at the end of the circulation in serum as previously applied to bacteriophage (Merril et al., 1996, Long-circulating bacteriophage as antibacterial agents, PNAS 93: 3188-3192), expressly incorporated herein by reference in its entirety. The selection may be performed in live animals, including mice, rats, guinea pigs, rabbits, pigs, dogs, cats, monkeys and human volunteers. The procedure may also be carried out in vitro, using blood from any of the above donors by successive passages and isolation of individual colonies resistant to complement and/or other serum components.

5.6.2. Expression of serum-resistance genes. Expression or over-expression of serum resistance genes can be accomplished by conventional heterologous expression methods known to those skilled in the arts. The serum resistome of *E. coli* has been described (Phan et al., 2013 The serum resistome of a globally disseminated multidrug resistant uropathogenic *Escherichia coli* clone, PLoS Genetics DOI: 10.1371/journal.pgen.1003834, incorporated by reference in its entirety). Serum resistance genes also include the *Salmonella* Rck (resistance to complement killing) and PagC proteins or its homologues from *E. coli* (Lom) *Yersinia* entercolitica (ail) and *Enterobacter cloacae* (OmpX) (Heffernan E J, et al., 1992. The *Salmonella typhimurium* virulence plasmid complement resistance gene rck is homologous to a family of virulence-related outer membrane protein genes, including pagC and ail. J. Bacteriol. 174: 84-91; Ho et al., 2011, Functional Recruitment of Human Complement Inhibitor C4b-Binding Protein to Outer Membrane Protein Rck of *Salmonella* PLoS ONE 6(11): e27546. doi:10.1371/journal.pone.0027546), Cirillo D M, et al., 1996. Identification of a domain in Rck, a product of the *Salmonella typhimurium* virulence plasmid, required for both serum resistance and cell invasion. Infect. Immun. 64: 2019-2023), each of which is expressly incorporated herein by reference in its entirety. Antibodies to Rck may also be used to select strains with increased expression. Resistance can also be obtained by expression of other genes, such as the melittin resitance gene pqaB (Baker et al., 1999, The *Salmonella typhi* melittin resistance gene pqaB affects intracellular growth in PMA-differentiated U937 cells, Polymyxin B resistance and lipopolysaccharide, Microbiology 145: 367-378), expressly incorporated herein by reference in its entirety. Furthermore, when the melittin resistance gene is expressed, the lytic protein melittin or melittin conjugates to targeted peptides may be used as antitumor agents (Liu et al., 2013, A novel melittin-MhIL-2 fusion protein inhibits the growth of human ovarian cancer SKOV3 cells in vitro and in vivo tumor growth, Cancer Immunol. Immunotherapy 62: 889-895), expressly incorporated herein by reference in its entirety. Other targeting peptides fused to melittin may be any of those from the references herein.

6. FIGURE LEGEND

The figures show compositions and methods to modify bacteria of the present technology.

FIGS. 1A-1C. Bacteria with reduced size. FIG. 1A. The mechanism for selecting bacteria with reduced size by passage of a population of bacteria containing spontaneous mutants, induced mutants and/or suppressor mutants through progressively smaller syringe cartridge microporous filters of 0.65, 0.45 and 0.22 μm. FIG. 1B. Facilitation of reduced size bacteria by genome reduction. Following genome reduction methods, the bacteria may be selected for reduced size as shown in FIG. 1A. FIG. 1C. Facilitation of reduced size bacteria by genome compaction through addition of histone-like proteins from Chalamydia and the appropriate target sequence. Following genome reduction methods, the bacteria may be selected for reduced size as shown in FIG. 1A. The process may be further combined with the method of FIG. 1B.

FIGS. 2A-2C. Bacteria with a protective sialic acid coat. FIG. 2A. The genes necessary for LPS sialyation are cloned into and expressed by the bacteria, resulting in the LPS O-antigen being sialyated (Severi et al., 2007, Sialic acid utilization by bacterial pathogens, Microbiology 153: 2817-2822, expressly incorporated herein by reference in its entirety). FIG. 2B. The genes necessary for PSA capsule biosynthesis and export are cloned into and expressed by the bacteria, resulting in a sialic acid capsule. FIG. 2C. The genes for sialic acid scavenging and utilization are cloned into and expressed by the bacteria, resulting in the LPS O-antigen being sialyated.

FIGS. 3A-3C Bacteria with inducible expression of alternate surface antigens. FIG. 3A. The wild type rfb gene cluster and rfc gene encoding the O: 1, 4, 5, 12 antigen, and the wild type H1 flagellar antigen, all with wild type promoters. FIG. 3B. Three different rfb gene cluster with the rfc gene encoding the O: 1, 4, 5, 12 antigens, and the H1 flagellar antigen under control of the sulA (x-ray inducible) promoter; the O: 6, 7 antigens, and the H2 flagellar antigen under control of the tet (tetracycline) inducible promoter, and; the O: 3, 15, 34 antigens and the H3 flagellar antigen under control of the ara (arabinose) inducible promoter. Successive treatment with X-rays, tetracycline and arabinose respectively results in alternate expression of non-overlapping surface antigens. FIG. 3C. the mar regulon which consists of the mar promoter/operator, the MarR negative regulatory gene, the MarA positive regulatory gene, and a downstream start codon (ATG) which would normally comprise the start of the MarB coding sequence, which is used for the rfb O-antigen gene cluster. Alternatively the MarA regulon may be used for inducible expression of other anti-cancer effector genes.

Figure 4:
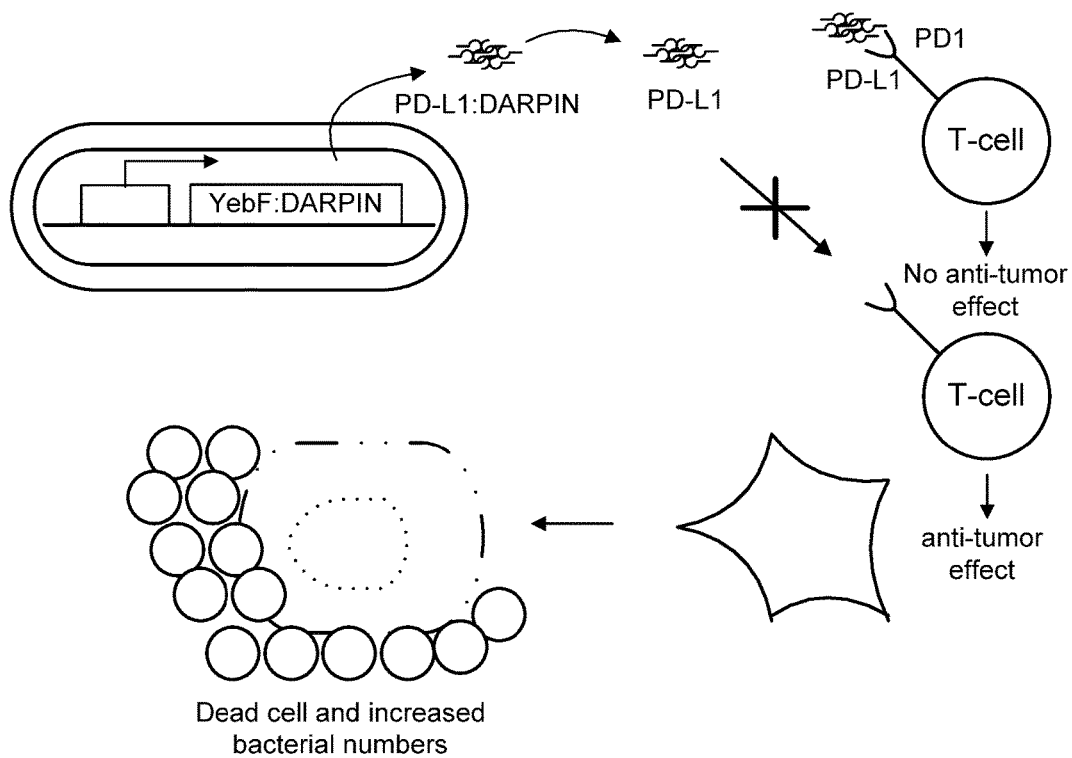
FIG. 4 shows bacteria delivering ligands against PD-1 ligand (PDL-1).

FIG. 4. Bacteria delivering ligands against PD-1 ligand (PD-L1). Bacteria expressing a PD-L1 agonist (a YebF fusion of an anti-PD-L1 DARPin) results in blocking the PD-L1 signal, thereby activating T-cells that destroy tumor cells and increase the number of bacteria within the tumor.

Figure 5:
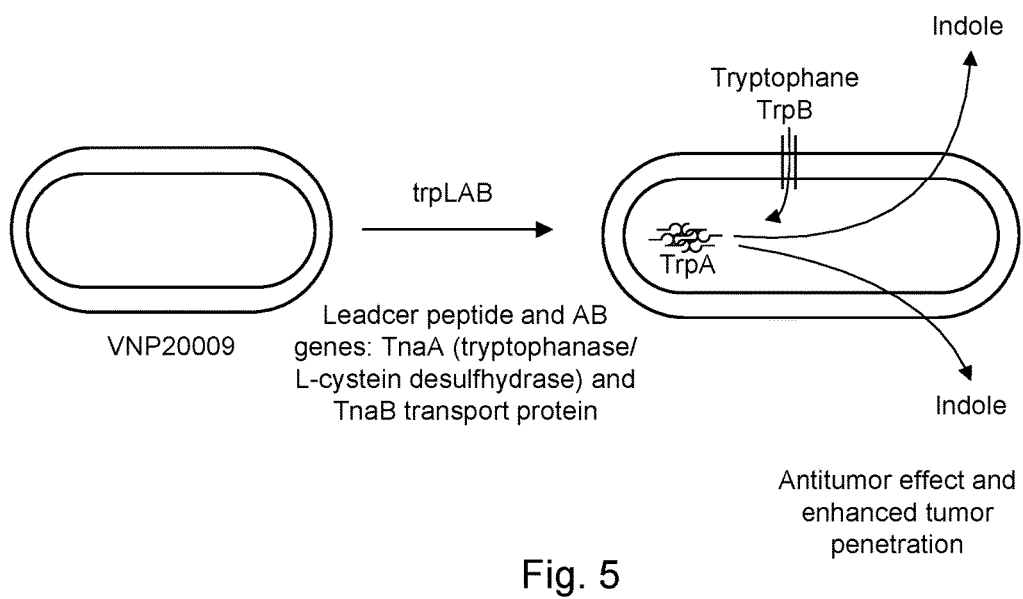
FIG. 5 shows bacteria that express the *E. coli* tryptophanase.

FIG. 5 shows bacteria that express the *E. coli* tryptophanase. The operon for tryptophanase including trypLAB are cloned and expressed in the bacteria, resulting in tumor cell toxicity, antitumor activity and increased tumor penetration of the bacteria.

7. EXAMPLES

In order to more fully illustrate the invention, the following examples are provided.

Example 1

Isolation of bacteria with reduced size based on spontaneous mutagenesis.

By way of example, the attenuated antineoplastic bacteria, or precursors to antineoplastic bacteria, are selected from a pool of mutants. The mutants may either be those that are spontaneous within a normal genetic background (i.e., a normal population), spontaneous mutants in a non-suppressed environmentally sensitive genetic background (e.g., msbB⁻), or spontaneous mutants within a mutator background. Bacteria of a normal genetic background and mutator backgrounds (e.g., mutL, mutS, mutH, alone or in combination) are grown from low density, e.g., a single colony inoculated into 100 ml of standard media such as Luria broth. Bacteria of an environmentally sensitive genetic background, such as strain YS1 (Murray et al., 2001, Extragenic suppressors of msbB⁻ growth defects in *Salmonella*. J. Bacteriol. 183: 5554-5561, expressly incorporated herein by reference in its entirety) are grown from low density, e.g., a single colony inoculated into 100 ml of media wherein the media contains a substance to which the bacteria are sensitive, such as 6 mM EGTA.

Bacteria with reduced size are selected for by passage through successively smaller pore sizes. Selection begins with passage through a 0.65 µM filter. Bacteria obtained this way are rechecked by repassage through the filter, with a high percentage of passage indicating bacteria with smaller size. These bacteria are then again subjected to the initial growth conditions above and then again selected for passage through a filter except that a 0.45 µM pore size is used. The process is then repeated for a 0.22 µM pore size. The mutations resulting in the bacteria passing through smaller pore sizes are determined by standard genetic means (Murray et al., 2001) or by genome sequencing.

Example 2

Isolation of bacteria with reduced size based on random mutagenesis.

The selection process described above is applied to bacteria that have been randomly mutagenized. Random mutagenesis can consist of either chemically/physically induced mutations such as those caused by nitrosoguanidine and ultraviolet light (Pawelek et al., 1997). The selection process described above is applied to bacteria that have been randomly mutagenized.

Example 3

Generation of bacteria with a protective sialic acid coat.

Figure 2A:
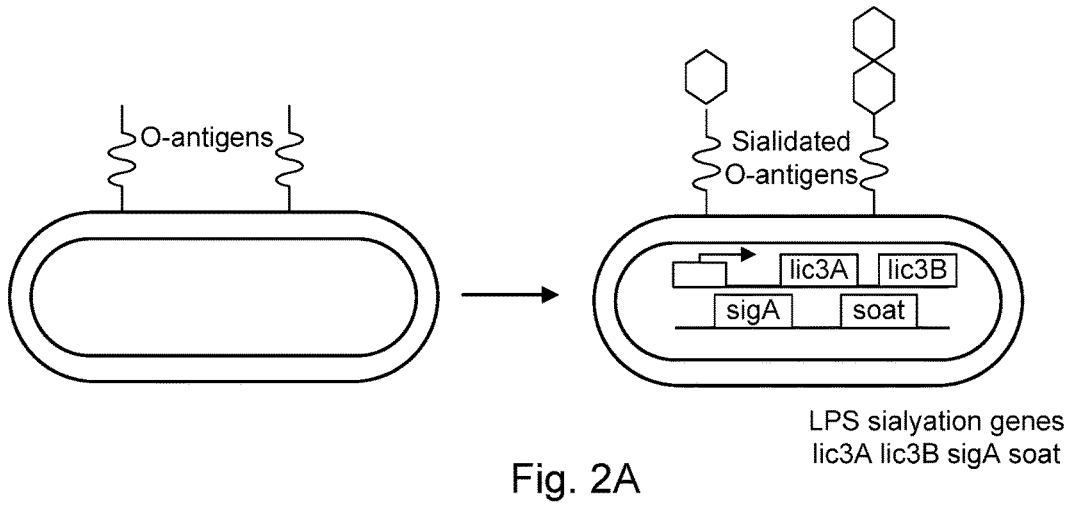
FIGS. 2A-2C show bacteria with a protective sialic acid coat.
Figure 2B:
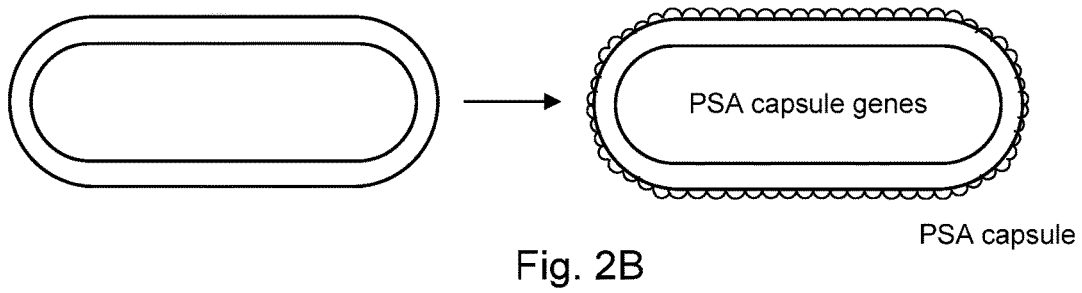
Figure 2C:
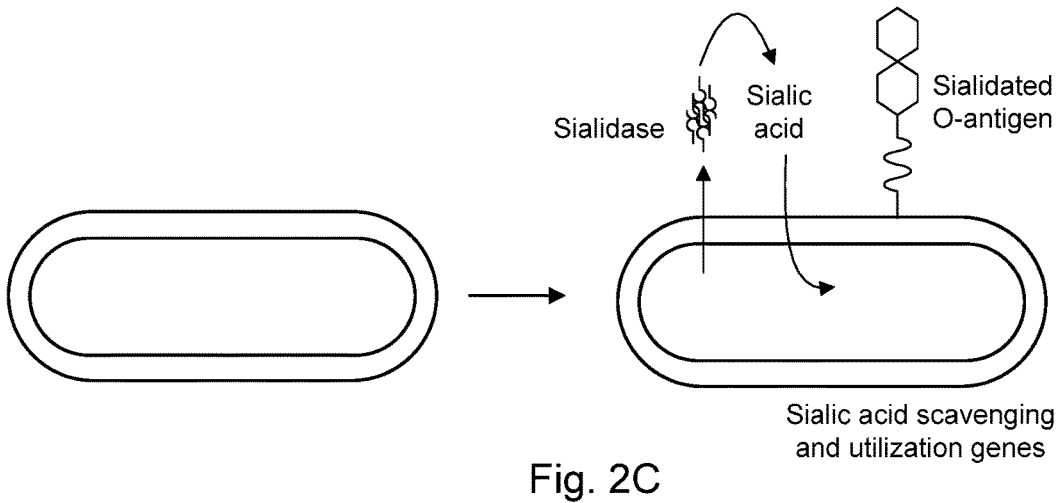

De novo synthesis of lipopolysaccharide with sialic acid is accomplished by heterologous expression of NeuA, NeuB, NeuC, SiaB, Lic3A, Lic3B, and SOAT (sialic acid O-acyltransferase) (Severi et al., 2007, Sialic acid utilization by bacterial pathogens, Microbiology 153: 2817-2822, expressly incorporated herein by reference in its entirety) as shown in FIGS. 2A-2C. Heterologous expression is achieved using synthetic biology and methods known to those skilled in the arts, including the methods described by King et al., 2009 (Tumor-targeted *Salmonella typhimurium* overexpressing cytosine deaminase: a novel, tumor-selective therapy, Meth. Mol. Biol. 542: 649-659), expressly incorporated herein by reference in its entirety. Induction of the sialic acid coat may be performed in vitro during manufacturing, or in vivo, following systemic administration.

Example 4

Generation of bacteria with inducible expression of alternate surface antigens.

Figure 3A:
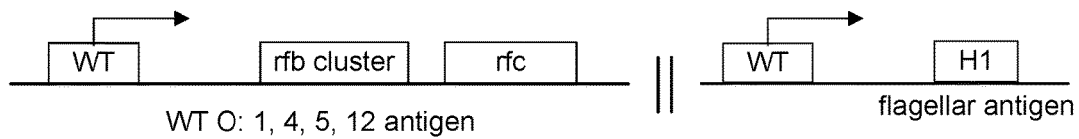
FIGS. 3A-3C show bacteria with inducible expression of alternate surface antigens, and the Mar regulon for use as an inducible promoter.
Figure 3B:
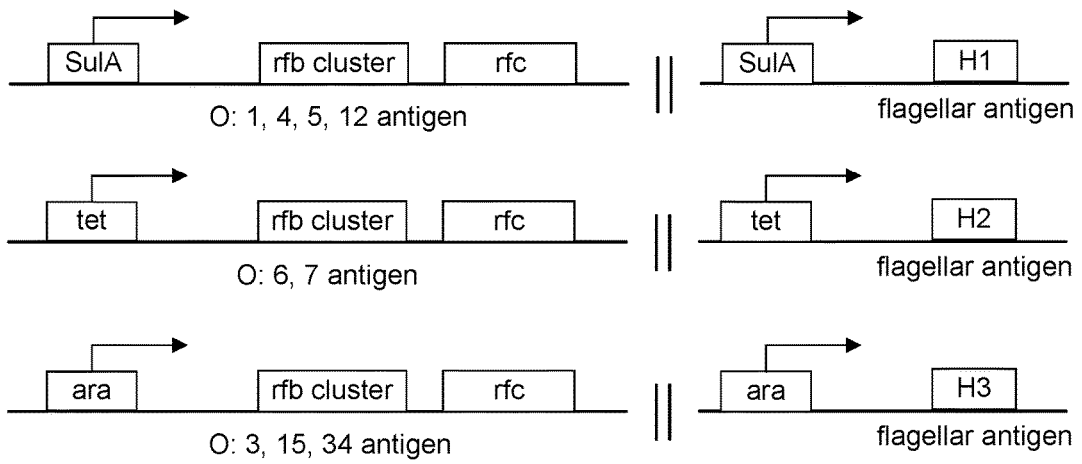
Figure 3C:
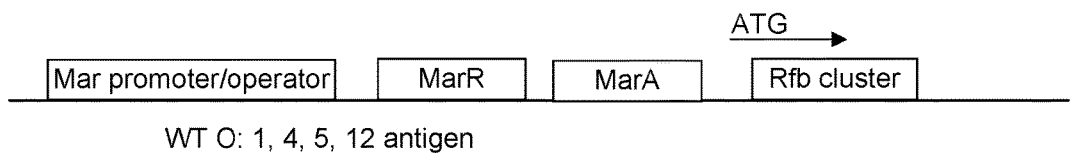

Methods for deriving heterologous O-antigens include methods known to those skilled in the arts, including those described by Favre et al., WO/1997/014782, and Roland WO/2000/004919, each of which is expressly incorporated herein by reference in its entirety. O-antigen synthesis is directed by the rfb gene cluster which encodes enzymes involved in biosynthesis of the monomer sugar unit, and the rfc gene, which encodes the O-antigen polymerase responsible for the polymerization of the sugar unit into a high molecular weight polysaccharide chain (Sugiyama et al., 1991 Expression of the Cloned *Escherichia coli* 09 rfb Gene in Various Mutant Strains of *Salmonella typhimurium*, J. Bacteriol. 173:55-58; Collins et al. 1991, Molecular Cloning, Characterization, and Nucleotide Sequence of the rfc Gene, Which Encodes an O-Antigen Polymerase of *Salmonella typhimurium*, J. Bacteriol. 173:2521-2529), each of which is expressly incorporated herein by reference in its entirety. The antigens are chosen such that alternate expression does not have overlap. For example the O-antigens of the *S. typhimurium* serovar are O: 1, 4, 5, 12, whereas those of *S. Montevideo*, O: 6, 7, and those of $E_3$ group are O: 3, 15, 34. The rfb gene cluster and rfc gene may be part of a single synthetic operon (polycistronic), or may be separate, monocystronic constructs, with separate individual promoters of the same type used to drive the expression of their respective genes. Use of separate inducible promoter for more than one antigen allows for their expression to occur simultaneously, sequentially, or alternating (repeated) depending upon which inducers are administer (FIGS. 3A-3C). Thus, to achieve multiple alternating sets of antigens, coexistance of a set of alternative, non-overlapping under control of a separate inducible promoter are constructed. Thus, a bacterial culture may be induced to have one set of antigens for a first injection, and may be induced to have a second set of antigens for a second injection, and so on. Similarly, following a first injection with induced expression of one set of antigens, the first inducer may be curtailed, and the inducer for the second set of antigens initiated, thus avoiding prolonged exposure to the immune systems and avoiding immune elimination.

Example 5

Generation of bacteria delivering ligands against PD-1 ligand (PDL-1).

Ligands against PDL1 include antibodies, affibodies (protein A affinity-based ligands), adnectins, anticalins and DARPins (designed ankyrin repeat proteins). Ligands against PDL1 such as affibodies and DARPins are expressed using secretion proteins described above, such as fusions with YebF (FIG. 4). Affibodies are generated as described by Felwisch and Tomachev 2012, Enginnering of affibody molecules for therapy and diagnosis. Methods Molecular Biol 899: 103-126). DARPins are designed and screened for as previously described (Stumpp and Amstutz 2007, DARPins: a true alternative to antibodies, Curr Opin Drug Discov. Devel. 10: 159-153; Zahnd et al., 2010, Efficient tumor targeting with high-affinity designed ankyrin repeat proteins: Effects of Affinity and Molecular Size, Cancer Res 2010; 70:1595-1605; WO/2013022091 Therapeutic Agent For Autoimmune Diseases Comprising PD-1 Agonist), each of which is expressly incorporated herein by reference in its entirety. Combination with smaller size bacteria, alternating surface antigens and tryptophanase (see below) further enhance the overall antitumor effect.

Example 6

Generation of Bacteria that Express the *E. coli* Tryptophanase.

Expression of tryptophanase and demonstration of enhanced antitumor activity may be conducted as follows. Cloning of the tryptophanase operon uses methods known to those skilled in the arts, including PCR-based cloning (Forward primer=Tryp Kpn Nsi F1 TCggtacccAGGAGGAAttcaCCATGCATaatatcttacatatatgtgtgAcctcaaaat SEQ ID NO: 008 and reverse primer=Tryp Xba R1 gatcTCTAGAgaaggatTTAgccaaatttaggtaacac SEQ ID NO: 009). Cloning into an expression vector such as a modified pTrc99a with the arabinose promoter

```
                                            SEQ ID NO: 010
GGGGGCGGCCGCAAGAAACCAATTGTCCATATTGCATCAGACATTGCCGT

CACTGCGTCTTTTACTGGCTCTTCTCGCTAACCAAACCGGTAACCCCGCT

TATTAAAAGCATTCTGTAACAAAGCGGGACCAAAGCCATGACAAAAACGC

GTAACAAAAGTGTCTATAATCACGGCAGAAAAGTCCACATTGATTATTTG

CACGGCGTCACACTTTGCTATGCCATAGCATTTTTATCCATAAGATTAGC

GGATCCTACCTGACGCTTTTTATCGCAACTCTCTACTGTTTCTCCATACC

CGTTTTTTTGGGCTAGCGAATTCGAGCTCGGTACCCAGGAGGAATTCACC

ATGGAATTCGAGCTCGGTACCCGGGGATCCTCTAGAGTCGACCTGCAGGC

ATGCAAGCTTGGCTGTTTTGGCGGATGAGAGAAGATTTTCAGCCTGATAC

AGATTAAATCAGAACGCAGAAGCGGTCTGATAAAACAGAATTTGCCTGGC

GGCAGTAGCGCGGTGGTCCCACCTGACCCCATGCCGAACTCAGAAGTGAA

ACGCCGTAGCGCCGATGGTAGTGTGGGGTCTCCCCATGCGAGAGTAGGGA

ACTGCCAGGCATCAAATAAAACGAAAGGCTCAGTCGAAAGACTGGGCCTT

TCGTTTTATCTGTTGTTTGTCGGTGAACGCTCTCCTGAGTAGGACAAATC

CGCCGGGAGCGGATTTGAACGTTGCGAAGCAACGGCCCGGAGGGTGGCGG

GCAGGACGCCCGCCATAAACTGCCAGGCATCAAATTAAGCAGAAGGCCAT

CCTGACGGATGGCCTTTTTGCGTTTCTACAAACTCTTTTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTGTTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTACAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCTGATGCGGTATTTT

CTCCTTACGCATCTGTGCGGTATTTCACACCGCATATG
``` using KpnI and XbaI restriction endonucleases operably links the inducible ara promoter to a start codon (ATG) and results in a polycistronic message that produces all three peptides.

Successful expression of tryptophanase is determined by the addition of Kovac's reagent, which consists of isoamyl alcohol and par-dimethylaminobenzaldhyde in concentrated hydrochloric acid; a positive reaction is indicated by a red color. Determination of antitumor activity is performed according to the methods of Pawelek et al. (1997, Tumor-targeted *Salmonella* as a novel anticancer vector, Cancer Research 57: 4537-4544), expressly incorporated herein by reference in its entirety, with one control being mice bearing melanoma tumors without any treatment, a second control being the parental *salmonella* VNP20009 without the tryptophanase, and a test group consisting of the VNP20009 expressing the tryptophanase. The expression plasmid is transformed to a suitable *Salmonella* strain, such as VNP20009 (Low, et al., 2004, Construction of VNP20009, a novel, genetically stable antibiotic sensitive strain of tumor-targeting *Salmonella* for parenteral administration in humans, Methods Mol Med 90: 47-60) and used to treat mice for preclinical studies (Pawelek et al., 1997, Tumor-targeted *Salmonella* as a novel anticancer agent, Cancer Research 57: 4537-4544; Low et al., 1999, Lipid A mutant *salmonella* with suppressed virulence and TNF-alpha induction retain tumor-targeting in vivo, Nature Biotechnol. 17: 37-41; Lossner et al., 2007, Cell Microbiol. 9: 1529-1537; WO/2006/048344; Swofford et al., 2014 Biotechnology and Bioengineering 111: 1233-1245), and humans for clinical studies (Toso et al., 2002, Phase I study of the intravenous administration of attenuated *Salmonella typhimurium* to patients with metastatic melanoma, J. Clin. Oncol 20: 142-152), each of which is expressly incorporated herein by reference in its entirety.

Example 7

Selection of Bacteria with Increased Serum Survival and Increased Circulation Time.

Bacteria with increased serum circulation time are selected from natural populations, mutagenized populations, suppressed strains, partially suppressed strains, as described above. By way of specific example, strains with improved serum half-life may be selected for starting with the clinical strain VNP20009.

VNP20009 are injected into a 20 g mouse at $1\times10^6$ CFU/mouse. Bacteria are periodically sampled from blood, at 15 min, 30 min, 60 min, 120 min, 240 min, 480 min, 960 min, 1920 min and plated by serial dilutions of $10^0$-$10^{-6}$ and incubated overnight at 37 C. The next day, bacteria are selected from 1) the longest time point with viable bacteria and 2) from the longest time point at the highest dilution. All the bacteria on the plate from the longest time point and the highest dilution are pooled, grown overnight (approx. $10^9$ CFU/ml) and reinjected at the original concentration, and reisolated using the times and plating as above. The process may then be repeated. Individual bacteria from the plate from the longest time point and the highest dilution are then individually tested and compared to other bacteria from the same plate, and to the original VNP20009. Bacteria with at least a 30% increase, more preferably a 50% increase, and more preferably a 100% increase, and more preferably a greater than 100% increase are useful for antitumor studies (Pawelek et al., 1997). The above process may be repeated with a weight-adjusted dose, for rats, guinea pigs, rabbits, dogs, cats, pigs, monkeys or human volunteers. The process may also be scaled for the blood volume of a mouse (approx. 3 ml) to use of ex vivo human blood in vivo using sizes dependent upon availability and convenience. Ex vivo blood studies may also be performed, for example, in vacutainers, or in a chemostat using continuous fresh venous blood.

Example 8

Selection of Bacteria with Increased Survival in Blood with High CO2

Bacteria with increased survival in blood with high $CO_2$ are selected from natural populations, mutagenized populations, suppressed strains, partially suppressed strains, as described above. By way of specific example, strains with improved serum half-life may be selected for starting with the clinical strain VNP20009.

VNP20009 are injected into a 20 g mouse at $1\times10^6$ CFU/mouse, and the mice are exposed to carbogen (oxygen; 70% CO2 30%, or variations thereof). Bacteria are periodically sampled from blood, at 15 min, 30 min, 60 min, 120 min, 240 min, 480 min, 960 min, 1920 min and plated by serial dilutions of $10^0$-$10^{-6}$ and incubated overnight at 37 C. The next day, bacteria are selected from 1) the longest time point with viable bacteria and 2) from the longest time point at the highest dilution. All the bacteria on the plate from the longest time point and the highest dilution are pooled, grown overnight (approx. $10^9$ CFU/ml) and reinjected at the original concentration, and reisolated using the times and plating as above. The process may then be repeated. Individual bacteria from the plate from the longest time point and the highest dilution are then individually tested and compared to other bacteria from the same plate, and to the original VNP20009. Bacteria with at least a 30% increase, more preferably a 50% increase, and more preferably a 100% increase, and more preferably a greater than 100% increase are useful for antitumor studies (Pawelek et al., 1997). The above process may be repeated with a weight-adjusted dose, for rats, guinea pigs, rabbits, dogs, cats, pigs, monkeys or human volunteers. The process may also be scaled for the blood volume of a mouse (approx. 3 ml) to use of ex vivo human blood in vivo using sizes dependent upon availability and convenience. Ex vivo blood studies may also be performed, for example, in vacutainers, or in a chemostat using continuous fresh venous blood, and blood exposed to carbogen.

Example 9

Pharmaceutically Acceptable Formulations

Pharmaceutically acceptable formulations may be provided for delivery by other various routes e.g. by intramuscular injection, subcutaneous delivery, by intranasal delivery (e.g. WO 00/47222, U.S. Pat. No. 6,635,246), intradermal delivery (e.g. WO02/074336, WO02/067983, WO02/087494, WO02/0832149 WO04/016281, each of which is expressly incorporated herein by reference it its entirety) by transdermal delivery, by transcutaneous delivery, by topical routes, etc. Injection may involve a needle (including a microneedle), or may be needle-free. See, e.g., U.S. Pat. Nos. 7,452,531, 7,354,592, 6,962,696, 6,923,972, 6,863, 894, 6,685,935, 6,475,482, 6,447,784, 6,190,657, 6,080,849 and US Pub. 2003/0059400, each of which is expressly incorporated herein by reference.

Bacterial vector vaccines are known, and similar techniqaues may be used for the present bacteria as for bacterial vaccine vectors (U.S. Pat. No. 6,500,419, Curtiss, In: New Generation Vaccines: The Molecular Approach, Ed., Marcel Dekker, Inc., New York, N.Y., pages 161-188 and 269-288 (1989); and Mims et al, In: Medical Microbiology, Eds., Mosby-Year Book Europe Ltd., London (1993)). These known vaccines can enter the host, either orally, intranasally or parenterally. Once gaining access to the host, the bacterial vector vaccines express an engineered prokaryotic expression cassette contained therein that encodes a foreign antigen(s). Foreign antigens can be any protein (or part of a protein) or combination thereof from a bacterial, viral, or parasitic pathogen that has vaccine properties (New Generation Vaccines: The Molecular Approach, supra; Vaccines and Immunotherapy, supra; Hilleman, Dev. Biol. Stand., 82:3-20 (1994); Formal et al, Infect. Immun. 34:746-751 (1981); Gonzalez et al, J. Infect. Dis., 169:927-931 (1994); Stevenson et al, FEMS Lett., 28:317-320 (1985); Aggarwal et al, J. Exp. Med., 172:1083-1090 (1990); Hone et al, Microbial. Path., 5:407-418 (1988); Flynn et al, Mol. Microbiol., 4:2111-2118 (1990); Walker et al, Infect. Immun., 60:4260-4268 (1992); Cardenas et al, Vacc., 11:126-135 (1993); Curtiss et al, Dev. Biol. Stand., 82:23-33 (1994); Simonet et al, Infect. Immun., 62:863-867 (1994); Charbit et al, Vacc., 11:1221-1228 (1993); Turner et al, Infect. Immun., 61:5374-5380 (1993); Schodel et al, Infect. Immun., 62:1669-1676 (1994); Schodel et al, J. Immunol., 145:4317-4321 (1990); Stabel et al, Infect. Immun., 59:2941-2947 (1991); Brown, J. Infect. Dis., 155:86-92 (1987); Doggett et al, Infect. Immun., 61:1859-1866 (1993); Brett et al, Immunol., 80:306-312 (1993); Yang et al, J. Immunol., 145:2281-2285 (1990); Gao et al, Infect. Immun., 60:3780-3789 (1992); and Chatfield et al, Bio/Technology, 10:888-892 (1992)). Delivery of the foreign antigen to the host tissue using bacterial vector vaccines results in host immune responses against the foreign antigen, which provide protection against the pathogen from which the foreign antigen originates (Mims, The Pathogenesis of Infectious Disease, Academic Press, London (1987); and New Generation Vaccines: The Molecular Approach, supra). See also: Formal et al, Infect. Immun., 34:746-751 (1981); Wick et al, Infect. Immun., 62:4542-4548 (1994)); Hone et al, Vaccine, 9:810-816 (1991); Tacket et al, Infect. Immun., 60:536-541 (1992); Hone et al, J. Clin. Invest., 90:412-420 (1992); Chatfield et al, Vaccine, 10:8-11 (1992); Tacket et al, Vaccine, 10:443-446 (1992); van Damme et al, Gastroenterol., 103:520-531 (1992) (*Yersinia pestis*), Noriega et al, Infect. Immun., 62:5168-5172 (1994)(*Shigella* spp), Levine et al, In: *Vibrio cholerae*, Molecular to Global Perspectives, Wachsmuth et al, Eds, ASM Press, Washington, D.C., pages 395-414 (1994)(*Vibrio cholerae*), Lagranderie et al, Vaccine, 11:1283-1290 (1993); Flynn, Cell. Molec. Biol., 40(Suppl. 1):31-36 (1994)(*Mycobacterium* strain BCG), Schafer et al, J. Immunol., 149:53-59 (1992)(*Listeria monocytogenes*), each of which is expressly incorporated herein by reference.

The bacteria are generally administered along with a pharmaceutically acceptable carrier and/or diluent. The particular pharmaceutically acceptable carrier an/or diluent employed is not critical to the present invention unless otherwise specific herein (or in a respective incorporated referenced relevant to the issue). Examples of diluents include a phosphate buffered saline, buffer for buffering against gastric acid in the stomach, such as citrate buffer (pH 7.0) containing sucrose, bicarbonate buffer (pH 7.0) alone (Levine et al, J. Clin. Invest., 79:888-902 (1987); and Black et al J. Infect. Dis., 155:1260-1265 (1987), expressly incorporated herein by reference), or bicarbonate buffer (pH 7.0) containing ascorbic acid, lactose, and optionally aspartame (Levine et al, Lancet, 11:467-470 (1988), expressly incorporated herein by reference). Examples of carriers include proteins, e.g., as found in skim milk, sugars, e.g., sucrose, or polyvinylpyrrolidone. Typically these carriers would be used at a concentration of about 0.1-30% (w/v) but preferably at a range of 1-10% (w/v).

Set forth below are other pharmaceutically acceptable carriers or diluents which may be used for delivery specific routes. Any such carrier or diluent can be used for administration of the bacteria of the invention, so long as the bacteria are still capable of invading a target cell. In vitro or in vivo tests for invasiveness can be performed to determine appropriate diluents and carriers. The compositions of the invention can be formulated for a variety of types of administration, including systemic and topical or localized administration. Lyophilized forms are also included, so long as the bacteria are invasive upon contact with a target cell or upon administration to the subject. Techniques and formulations generally may be found in Remmington's Pharmaceutical Sciences, Meade Publishing Co., Easton, Pa., expressly incorporated herein by reference in its entirety. For systemic administration, injection is preferred, including intramuscular, intravenous, intraperitoneal, and subcutaneous. For injection, the composition, e.g., bacteria, of the invention can be formulated in liquid solutions, preferably in physiologically compatible buffers such as Hank's solution or Ringer's solution.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner.

For administration by inhalation, the pharmaceutical compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the composition, e.g., bacteria, and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The pharmaceutical compositions may also be formulated in rectal, intravaginal or intraurethral compositions such as suppositories or retention enemas, e.g., containing conventional suppository bases such as cocoa butter or other glycerides.

See also U.S. Pat. No. 6,962,696, expressly incorporated herein by reference in its entirety.

The present invention provides a pharmaceutical composition comprising a pharmaceutically acceptable carrier and an attenuated tumor-targeted bacteria comprising one or more nucleic acid molecules encoding one or more primary effector molecules operably linked to one or more appropriate promoters. The present invention provides a pharmaceutical composition comprising a pharmaceutically acceptable carrier and an attenuated tumor-targeted bacteria comprising one or more nucleic acid molecules encoding one or more primary effector molecules and one or more secondary effector molecules operably linked to one or more appropriate promoters.

The present invention provides a pharmaceutical composition comprising a pharmaceutically acceptable carrier and a bacteria.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, and the like. Saline is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic attenuated tumor-targeted bacteria, in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a suspending agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the pharmaceutical composition of the invention which will be effective in the treatment or prevention of a solid tumor cancer will depend on the nature of the cancer, and can be determined by standard clinical techniques. In addition, in vitro assays may optionally be employed to help identify optimal dosage ranges. The precise dose to be employed in the formulation will also depend on the route of administration, and the seriousness of the cancer, and should be decided according to the judgment of the practitioner and each patient's circumstances. However, suitable dosage ranges are generally from about 1.0 c.f.u./kg to about $1 \times 10^{10}$ c.f.u./kg; optionally from about 1.0 c.f.u./kg to about $1 \times 10^8$ c.f.u./kg; optionally from about $1 \times 10^2$ c.f.u./kg to about $1 \times 10^8$ c.f.u./kg; optionally from about 1 $10^4$ c.f.u./kg to about $1 \times 10^8$ c.f.u./kg; and optionally from about $1 \times 10^4$ c.f.u./kg to about $1 \times 10^{10}$ c.f.u./kg. Effective doses may be extrapolated from dose-response curves derived from in vitro or animal model test systems.

Various delivery systems are known and can be used to administer a pharmaceutical composition of the present invention. Methods of introduction include but are not limited to intradermal, intramuscular, intraperitoneal, intravenous, subcutaneous, intrathecal, intranasal, epidural, and oral routes. Methods of introduction may also be intratumoral (e.g., by direct administration into the area of the tumor).

The compositions may be administered by any convenient route, for example by infusion or bolus injection, by absorption through epithelial or mucocutaneous linings (e.g., oral mucosa, rectal and intestinal-mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or preneoplastic tissue.

The attenuated tumor-targeted bacteria comprising one or more primary effector molecules and optionally, one or more secondary effector molecules may be delivered in a controlled release system. The attenuated tumor-targeted bacteria comprising one or more fusion proteins of the invention and optionally, one or more effector molecules may also be delivered in a controlled release system. In one embodiment, a pump may be used (see Langer, supra; Sefton, CRC Crit. Ref. Biomed. Eng. 14:201 (1987); Buchwald et al., 1980, Surgery 88:507; and Saudek et al., 1989, N. Engl. J. Med. 321:574), expressly incorporated herein by reference in their entirety. In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem: 23:61 (1983); see also Levy et al., 1985, Science 228:190; During et al., 1989, Ann. Neurol. 25:351; and Howard et al., 1989, J. Neurosurg. 71:105, expressly incorporated herein by reference in their entirety). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984), expressly incorporated by reference in its entirety).

Other controlled release systems are discussed in the review by Langer (1990, Science 249:1527-1533, expressly incorporated herein by reference in its entirety) and may be used in connection with the administration of the attenuated tumor-targeted bacteria comprising one or more primary effector molecule(s) and optionally, one or more secondary effector molecule(s).

The invention also provides a pharmaceutical pack or kit comprising one or more containers filled with one or more of the ingredients of the pharmaceutical compositions of the invention. Optionally associated with such container(s) can be a notice in the form prescribed by governmental agency regulating the manufacture, use or sale of pharmaceuticals or biological products, which notice reflects approval by the agency of manufacture, use or sale for human administration.

The present invention also provides methods for treating a solid tumor comprising administering to a human or animal in need thereof, a pharmaceutical composition of the invention and at least one other known cancer therapy. In a specific embodiment, a human or animal with a solid tumor cancer is administered a pharmaceutical composition of the invention and at least one chemotherapeutic agent. Examples of chemotherapeutic agents include, but are not limited to, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologs, and cytoxan.

The present invention includes the sequential or concomitant administration of pharmaceutical composition of the invention and an anti-cancer agent such as a chemotherapeutic agent. In a specific embodiment, the pharmaceutical composition of the invention is administered prior to (e.g., 2 hours, 6 hours, 12 hours, 1 day, 4 days, 6 days, 12 days, 14 days, 1 month or several months before) the administration of the anti-cancer agent. In another specific embodiment, the pharmaceutical composition of the invention is administered subsequent to (e.g., 2 hours, 6 hours, 12 hours, 1 day, 4 days, 6 days, 12 days, 14 days, 1 month or several months after) the administration of an anti-cancer agent. In a specific embodiment, the pharmaceutical composition of the invention is administered concomitantly with an anti-cancer agent. The invention encompasses combinations of anti-cancer agents and attenuated tumor-targeted bacteria engineered to express one or more nucleic acid molecules encoding one or more effector molecules and/or fusion proteins that are additive or synergistic.

The invention also encompasses combinations of anti-cancer agents and attenuated tumor-targeted bacteria engineered to express one or more nucleic acid molecules encoding one or more effector molecules and/or fusion proteins that have different sites of action. Such a combination provides an improved therapy based on the dual action of these therapeutics whether the combination is synergistic or additive. Thus, the novel combinational therapy of the present invention yields improved efficacy over either agent used as a single-agent therapy.

In one embodiment, an animal with a solid tumor cancer is administered a pharmaceutical composition of the invention and treated with radiation therapy (e.g., gamma radiation or x-ray radiation). In a specific embodiment, the invention provides a method to treat or prevent cancer that has shown to be refractory to radiation therapy. The pharmaceutical composition may be administered concurrently with radiation therapy. Alternatively, radiation therapy may be administered subsequent to administration of a pharmaceutical composition of the invention, preferably at least an hour, five hours, 12 hours, a day, a week, a month, more preferably several months (e.g., up to three months), subsequent to administration of a pharmaceutical composition.

The radiation therapy administered prior to, concurrently with, or subsequent to the administration of the pharmaceutical composition of the invention can be administered by any method known in the art. Any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma ray emitting radioisotopes, such as radioactive isotopes of radium, cobalt and other elements may also be administered to expose tissues to radiation.

Additionally, the invention also provides methods of treatment of cancer with a Pharmaceutical composition as an alternative to radiation therapy where the radiation therapy has proven or may prove too toxic, i.e., results in unacceptable or unbearable side effects, for the subject being treated.

The pharmaceutical compositions of the invention are preferably tested in vitro, and then in vivo for the desired therapeutic or prophylactic activity, prior to use in humans. For example, in vitro assays which can be used to determine whether administration of a specific pharmaceutical composition is indicated, include in vitro cell culture assays in which a patient tissue sample is grown in culture, and exposed to or otherwise administered a pharmaceutical composition, and the effect of such composition upon the tissue sample is observed.

Pharmaceutical compositions of the invention can be tested for their ability to augment activated immune cells by contacting immune cells with a test pharmaceutical composition or a control and determining the ability of the test pharmaceutical composition to modulate (e.g., increase) the biological activity of the immune cells. The ability of a test composition to modulate the biological activity of immune cells can be assessed by detecting the expression of cytokines or antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Cytokine and antigen expression can be assayed, for example, by immunoassays including, but are not limited to, competitive and non-competitive assay systems using techniques such as western blots, immunohisto-chemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A, immunoassays and FACS analysis. The activation of signaling molecules can be assayed, for example, by kinase assays and electromobility shift assays (EMSAs). The effector function of T-cells can be measured, for example, by a 51Cr-release assay (see, e.g., Palladino et al., 1987, Cancer Res. 47:5074-5079 and Blachere et al., 1993, J. Immunotherapy 14:352-356, expressly incorporated herein by reference).

Pharmaceutical compositions of the invention can be tested for their ability to reduce tumor formation in animals suffering from cancer. Pharmaceutical compositions of the invention can also be tested for their ability to alleviate of one or more symptoms associated with a solid tumor cancer. Further, pharmaceutical compositions of the invention can be tested for their ability to increase the survival period of patients suffering from a solid tumor cancer. Techniques known to those of skill in the art can be used to analyze the function of the pharmaceutical compostions of the invention in animals.

In various specific embodiments, in vitro assays can be carried out with representative cells of cell types involved in a solid tumor cancer, to determine if a pharmaceutical composition of the invention has a desired effect upon such cell types.

Pharmaceutical compositions of the invention for use in therapy can be tested in suitable animal model systems prior to testing in humans, including but not limited to rats, mice, chicken, cows, monkeys, pigs, dogs, rabbits, etc. For in vivo testing, prior to administration to humans, any animal model system known in the art may be used.

Each reference cited herein is expressly incorporated herein in its entirety. Such references provide examples representing aspects of the invention, uses of the invention, disclosure of the context of the invention and its use and application. The various aspects disclosed herein, including subject matter incorporated herein by reference, may be employed, in combination or subcombination and in various permutations, consistent with the claims.

The invention may be embodied in other specific forms without departing from its spirit or essential characteristics. The described embodiment is to be considered in all respects only illustrative and not restrictive. The scope of the invention is, therefore, indicated by the appended claims rather by the foregoing description. All changes that fall within the meaning and range of equivalency of the claims are to be embraced within their scope.

What is claimed is:

1. A method for treating a neoplastic disease causing a solid tumor having a necrotic region in a subject, comprising:
   administering a pharmaceutically acceptable formulation containing a live genetically engineered *Salmonella* bacterium having a sialic acid O-acyltransferase gene which facilitates carbohydrate decoration of external components of the genetically engineered *Salmonella* bacterium;
   permitting the live genetically engineered *Salmonella* bacterium to grow within the subject;
   clearing the live genetically engineered *Salmonella* bacterium from the subject after growing,
   wherein the growth and clearing of the live genetically engineered *Salmonella* bacterium are effective to cause antitumor effects which are non-lethal to the subject.

2. The method according to claim 1, wherein the live genetically engineered *Salmonella* bacterium produces sialic acid O-acyl transferase from the sialic acid O-acyltransferase gene under control of heterologous first inducible promoter.

3. The method according to claim 2, wherein the live genetically engineered *Salmonella* bacterium further comprises a second gene, producing a secreted functional antitumor enzyme under control of a second heterologous inducible promoter, being distinct from first inducible promoter.

4. The method according to claim 3, further comprising, after growth of the live genetically engineered *Salmonella* bacterium in the solid tumor of the subject, secreting by the genetically engineered bacterium the sialic acid O-acyl transferase under control of the first inducible promoter, for action on external components of the live genetically engineered *Salmonella* bacterium.

5. The method according to claim 4, further comprising, after growth of the live genetically engineered *Salmonella* bacterium in the solid tumor of the subject, secreting by from the genetically engineered *Salmonella* bacterium the secreted functional antitumor enzyme gene product under control of the second inducible promoter, for action against tumor cells.

6. The method according to claim 1, wherein the genetically engineered bacterium further produces and secretes O-antigen.

7. The method according to claim 1, further comprising producing and secreting an anti-tumor enzyme from the live genetically engineered bacterium in active form.

8. The method according to claim 7, wherein the anti-tumor enzyme comprises an amino-acid degrading enzyme.

9. The method according to claim 8, wherein the amino-acid degrading enzyme is tryptophanase.

10. The method according to claim 1, wherein the live genetically engineered *Salmonella* bacterium comprises a MarA inducible promoter, which is induced by presence of acetyl salicylic acid.

11. The method according to claim 1, wherein the live genetically engineered *Salmonella* bacterium comprises an inducible promoter responsive to at least one of tet, arabinose, hypoxia, a cellular SOS response promoter, X-rays, and mitomycin.

12. The method according to claim 1, wherein the live genetically engineered *Salmonella* bacterium comprises a plurality of different genes comprising sialic acid O-acyltransferase, which each cause or induce carbohydrate decoration of external components of the genetically engineered *Salmonella* bacterium.

13. The method according to claim 1, further comprising administering to the subject a pharmacological inducer which is not naturally found in the subject, configured to selectively induce the genetically engineered *Salmonella* bacterium to produce a gene product having antitumor effects.

14. The method according to claim 13, wherein the live genetically engineered *Salmonella* bacterium comprises an inducible antitumor gene under control of an inducer, and the sialic acid O-acyl transferase is inducible by the same inducer to cause the genetically engineered bacterium to produce sialic acid O-acyl transferase, which causes carbohydrate decoration of external components of the genetically engineered *Salmonella* bacterium.

15. The method according to claim 1, wherein the live genetically engineered *Salmonella* bacterium has a selective tropism for solid tumor in the subject, and said clearing comprises administering an antibiotic to the subject.

* * * * *